(12) United States Patent
Vazales et al.

(10) Patent No.: US 12,138,390 B2
(45) Date of Patent: Nov. 12, 2024

(54) ARTIFICIAL AIRWAY MANAGEMENT DEVICES, SYSTEMS AND METHODS

(71) Applicant: SunMed Group Holding, LLC, Grand Rapids, MI (US)

(72) Inventors: Brad Eugene Vazales, Petosky, MI (US); David Mark Chersky, San Ramon, CA (US)

(73) Assignee: SunMed Group Holdings, LLC, Grand Rapids, MI (US)

( * ) Notice: Subject to any disclaimer, the term of this patent is extended or adjusted under 35 U.S.C. 154(b) by 0 days.

(21) Appl. No.: 17/975,766

(22) Filed: Oct. 28, 2022

(65) Prior Publication Data

US 2023/0051727 A1    Feb. 16, 2023

Related U.S. Application Data

(63) Continuation of application No. 16/474,362, filed as application No. PCT/US2017/068711 on Dec. 28, 2017, now Pat. No. 11,541,195.
(Continued)

(51) Int. Cl.
*A61M 16/04*    (2006.01)
*A61B 1/12*    (2006.01)
*A61L 2/10*    (2006.01)

(52) U.S. Cl.
CPC ......... *A61M 16/0463* (2013.01); *A61B 1/122* (2013.01); *A61L 2/10* (2013.01);
(Continued)

(58) Field of Classification Search
CPC .. A61L 2/10; A61L 2202/11; A61L 2202/123; A61L 2202/14; A61L 2202/16;
(Continued)

(56) References Cited

U.S. PATENT DOCUMENTS 1,800,277 A    4/1931   Boerstler
5,300,043 A    4/1994   Devlin et al.
(Continued)

FOREIGN PATENT DOCUMENTS

EP          2 762 169 A1    8/2014
WO       WO 00/15276 A1    3/2000
(Continued)

OTHER PUBLICATIONS

International Search Report and Written Opinion for PCT/US17/68711, dated Mar. 7, 2018, 11 pages.
(Continued)

*Primary Examiner* — Sean E Conley
(74) *Attorney, Agent, or Firm* — Sheridan Ross P.C.

(57) ABSTRACT

Systems and methods for cleaning and maintaining artificial airways sized for insertion within pediatric or neonatal patients (e.g., external diameters of less than 5 mm) are disclosed. The system includes a multi-port ventilator manifold configured to couple to a ventilation source, thereby forming a ventilator circuit with the patient. The manifold includes an occluder configured to advantageously reduce an amount of dead space in the manifold so as to prevent less of positive end expiratory pressure of the ventilator circuit and reduce the likelihood of broncho-pulmonary dysplasia of the patient, or even premature death.

9 Claims, 14 Drawing Sheets

Related U.S. Application Data

(60) Provisional application No. 62/441,037, filed on Dec. 30, 2016.

(52) U.S. Cl.
CPC ...... *A61L 2202/11* (2013.01); *A61L 2202/123* (2013.01); *A61L 2202/14* (2013.01); *A61L 2202/16* (2013.01); *A61L 2202/17* (2013.01); *A61L 2202/24* (2013.01); *A61M 2205/053* (2013.01); *A61M 2209/10* (2013.01)

(58) Field of Classification Search
CPC ............ A61L 2202/17; A61L 2202/24; A61M 16/0463; A61B 1/22
See application file for complete search history.

(56) References Cited

U.S. PATENT DOCUMENTS

| | | | |
|---|---|---|---|
| 5,642,726 | A | 7/1997 | Owens et al. |
| 6,702,789 | B1 | 3/2004 | Owens et al. |
| 6,805,125 | B1 | 10/2004 | Crump et al. |
| 7,263,997 | B2 | 9/2007 | Madsen et al. |
| 8,955,518 | B2 | 2/2015 | Wondka |
| 9,056,147 | B2 | 6/2015 | Ma |
| 9,393,382 | B2 | 7/2016 | Heck |
| 9,592,374 | B2 | 3/2017 | Muse |
| 10,004,863 | B2 | 6/2018 | Vazales et al. |
| 10,112,024 | B2 | 10/2018 | Geraghty et al. |
| 10,279,057 | B2 | 5/2019 | Ma |
| 11,439,716 | B2 * | 9/2022 | Etter .................. A61L 2/26 |
| 11,541,195 | B2 | 1/2023 | Vazales et al. |
| 2004/0221842 | A1 | 11/2004 | Madsen et al. |
| 2007/0176117 | A1 * | 8/2007 | Redmond ............ A61M 39/16 250/455.11 |
| 2008/0159908 | A1 | 7/2008 | Redmond |
| 2010/0072399 | A1 | 3/2010 | Street et al. |
| 2010/0286657 | A1 | 11/2010 | Heck |
| 2011/0023885 | A1 | 2/2011 | Vazales et al. |
| 2012/0053512 | A1 | 3/2012 | Muse |
| 2012/0321509 | A1 | 12/2012 | Bak |
| 2013/0019864 | A1 | 1/2013 | Wondka |
| 2013/0104884 | A1 | 5/2013 | Vazales et al. |
| 2013/0323120 | A1 | 12/2013 | Ma |
| 2014/0150782 | A1 | 6/2014 | Vazales et al. |
| 2014/0334974 | A1 | 11/2014 | Rasooly et al. |
| 2016/0296719 | A1 | 10/2016 | Geraghty et al. |
| 2016/0324997 | A1 | 11/2016 | Dayton |

FOREIGN PATENT DOCUMENTS

| | | |
|---|---|---|
| WO | WO 2010/023329 | 3/2010 |
| WO | WO 2010/132429 A2 | 11/2010 |
| WO | WO 2011/020985 A1 | 2/2011 |
| WO | WO 2011/126812 | 10/2011 |
| WO | WO 2015/187583 A1 | 12/2015 |

OTHER PUBLICATIONS

Official Action for European Patent Application No. 20196320.4, dated Aug. 4, 2023 10 pages.
Official Action for U.S. Appl. No. 16/474,362, dated Jun. 15, 2022 15 pages.
Notice of Allowance for U.S. Appl. No. 16/474,362, dated Oct. 19, 2022 7 pages.
Intention to Grant for European Patent Application No. 17886533.3, dated Nov. 27, 2023 58 pages.
Intention to Grant for European Patent Application No. 20196320.4, dated Apr. 11, 2024 57 pages.

* cited by examiner

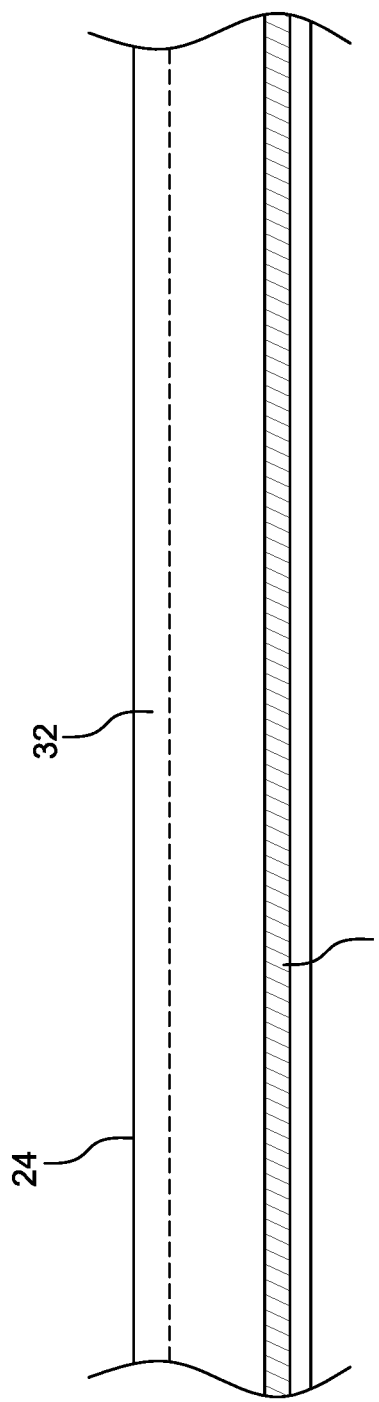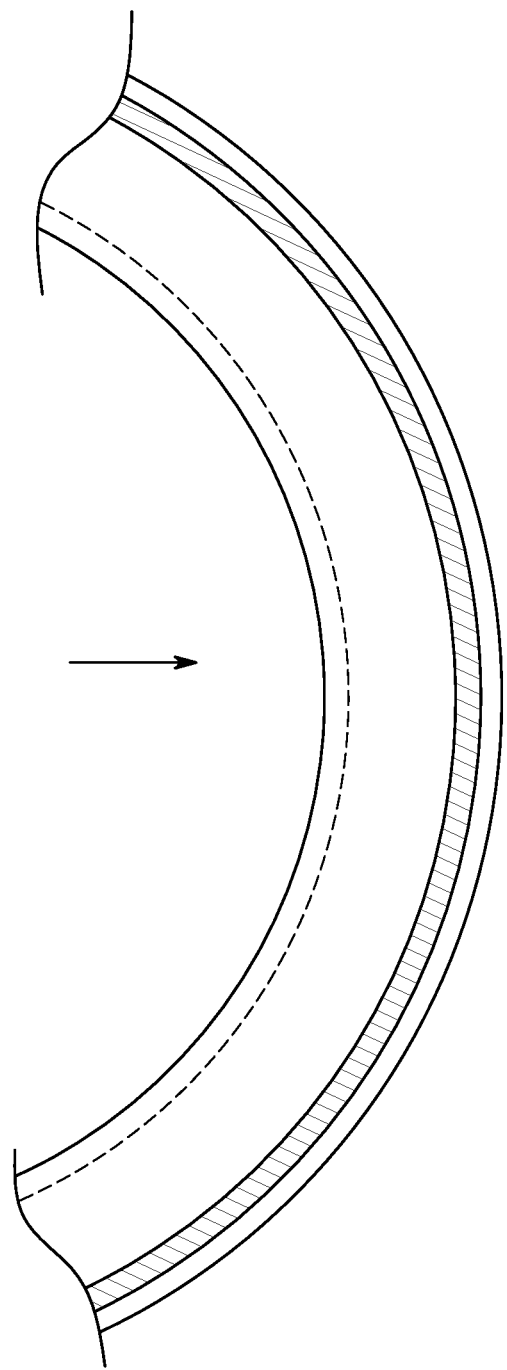

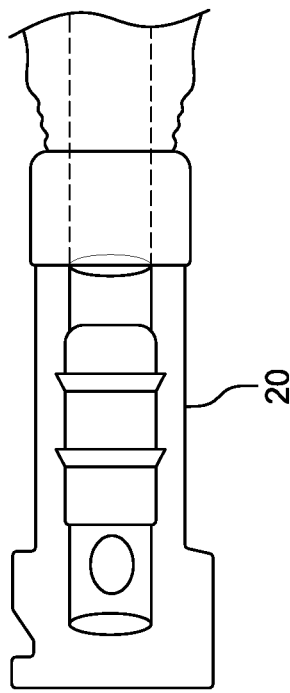
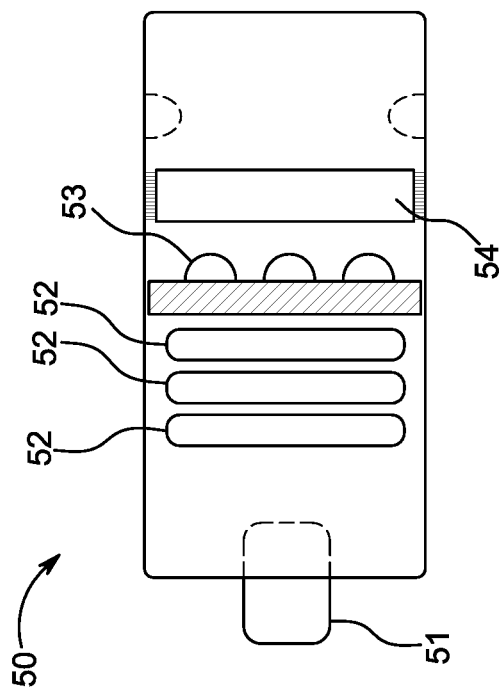
FIG. 5
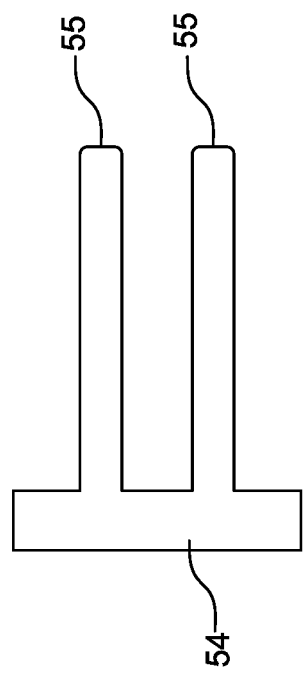
FIG. 5A

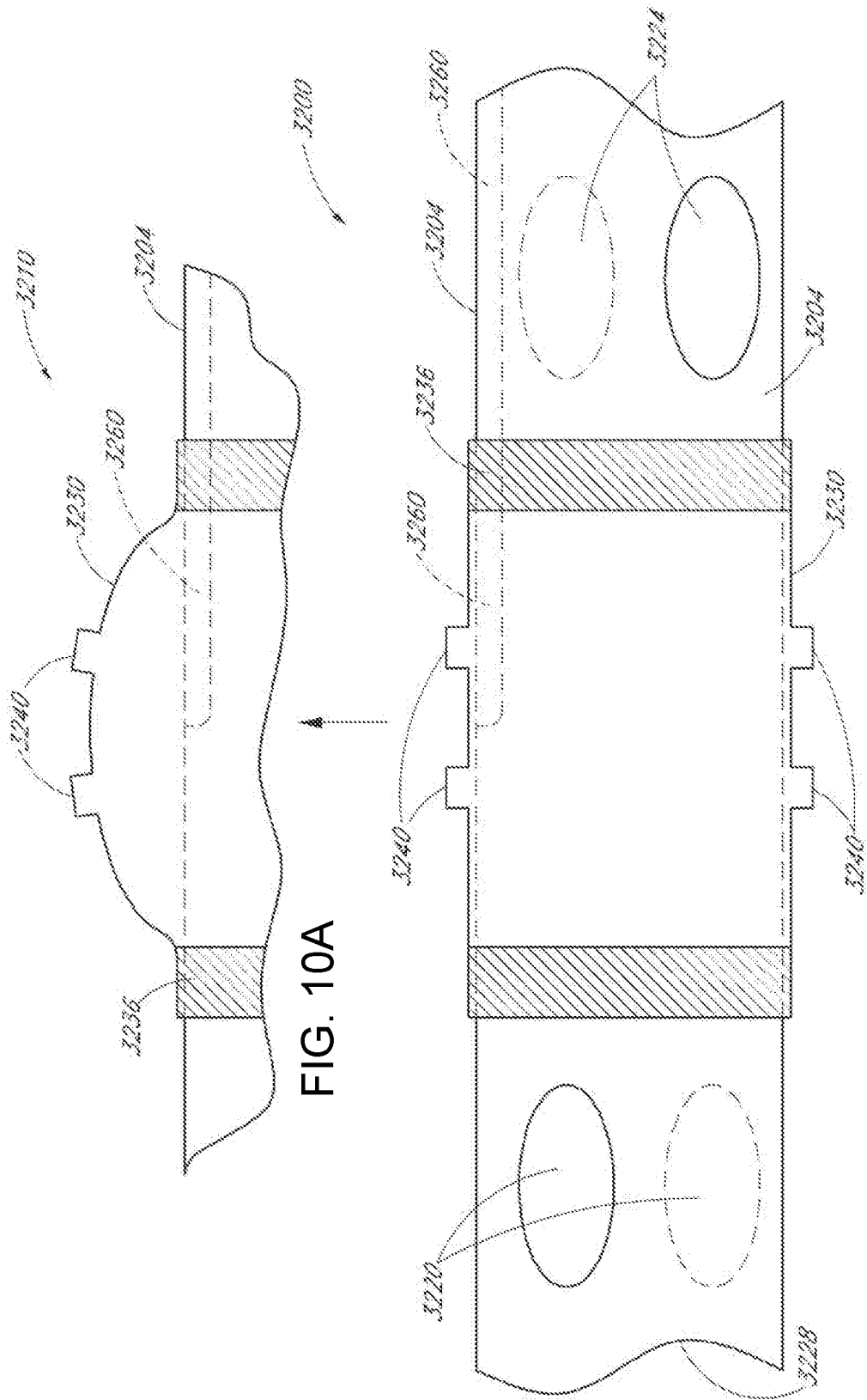

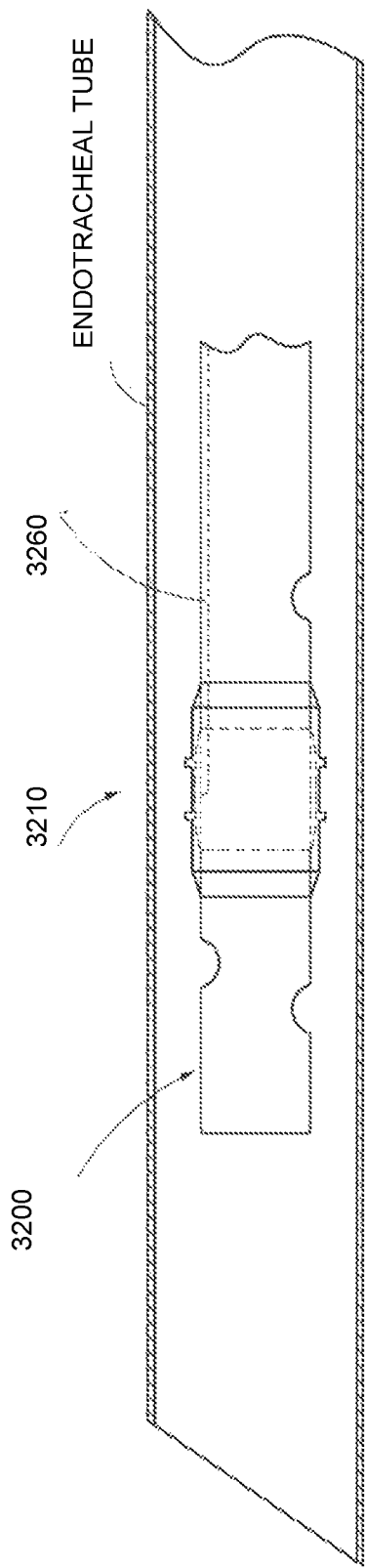
FIG. 11A
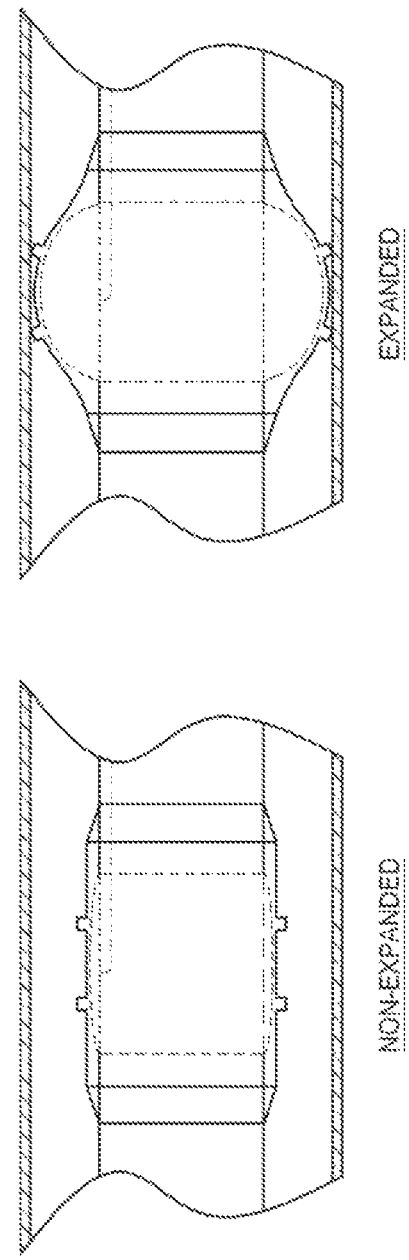
FIG. 11B
FIG. 11C

ARTIFICIAL AIRWAY MANAGEMENT DEVICES, SYSTEMS AND METHODS

RELATED APPLICATIONS

This application is a continuation of U.S. patent application Ser. No. 16/474,362 filed on Jun. 27, 2019, which is a National Stage entry of International Patent Application No. PCT/US2017/068711 filed Dec. 27, 2017, which claims priority to U.S. Provisional Patent Application No. 62/441,037 filed on Dec. 30, 2016, the entire contents of each of which are hereby incorporated by reference herein. International Patent Application No. PCT/US2017/068711 is related to PCT Publication No. WO 2015/187583, the entire content of which is hereby incorporated by reference herein.

FIELD

Embodiments disclosed herein relate generally to devices, systems and methods for cleaning of artificial airways or body-inserted tubes (e.g., endotracheal tubes) and/or for airway management.

BACKGROUND

During an intubation procedure, endotracheal tubes can be placed in patients who are unable to effectively maintain life-sustaining ventilation and respiration on their own. An endotracheal tube is used in patient care to ensure a clear airway through the mouth, pharynx, and trachea into the lungs. Use of an endotracheal tube is appropriate when the integrity of the airway is, or may become, challenged due to trauma or pathology, or if a patient cannot otherwise breathe unaided. Often the endotracheal tube is coupled to a mechanical ventilator to aid the patient's respiration, and can be expected to remain in situ for an extended time until the patient is once again able to breathe on his or her own. The endotracheal tubes can be inserted within a patient's native airway for short periods of time (e.g., for a matter of hours during anesthesia for surgery) or the endotracheal tubes can remain in place to provide ventilator-assisted breathing for days or weeks.

The institution of mechanical ventilation can result in increased production of secretions within the patient's native airways and accumulation of those secretions within an artificial airway such as an endotracheal tube. The insertion of an endotracheal tube within the patient's trachea renders the normal cough mechanism for clearing of secretions ineffective, as the patient cannot transiently close the glottis to build up pressure in the airway that, when released, helps expel secretions. Also, the mucociliary system which helps transport secretions and debris from the tracheobronchial tree into the trachea for expectoration becomes ineffective in the sick, intubated patient. The secretions, therefore, can pool in dependent portions of the lung over time due to gravity and, if not removed in a timely manner, can result in ventilator-acquired pneumonia (VAP) or other undesired conditions or ailments. Closed suction systems may be coupled to the endotracheal tube and a suction catheter may be used to suction out the pooled secretions or other debris within the patient's native airways and/or the endotracheal tube. Intraluminal volume loss attributable to the accumulation of secretions on the interior wall of endotracheal tubes is not prevented by standard suctioning treatment. Secretion accumulation can lead to life-threatening occlusion of the endotracheal tube or at least increased work of breathing, which may result in increased difficulty in weaning, and prolonged mechanical ventilation and intensive care unit stay, especially for neonatal and pediatric-sized endotracheal tubes. Additionally, secretion accumulation on the inside of the endotracheal tube leads to colonization with potentially pathological organisms and this colonization is likewise implicated in the development of VAP.

SUMMARY OF DISCLOSURE

In accordance with several embodiments, a system for maintenance of an artificial airway includes one or more cleaning modules (e.g., suction catheter module, endotracheal tube cleaning module, visualization module) adapted to be removably and interchangeably coupled to an access port of a manifold that is adapted to be coupled to a body-inserted medical tube (e.g., endotracheal tube). The manifold may include a ventilator port adapted to couple to a standard ventilation source (e.g., ventilator or ventilation unit) so as to provide ventilation to a patient from the ventilator through the artificial airway. The cleaning modules may include instruments configured to access and/or treat the artificial airway (e.g., endotracheal tube) and/or tracheobronchial tree. The access port of the manifold can be reversibly closed (e.g., via an occluder such as a stopcock or barrier valve that can rotate in and out of an occluding or blocking configuration) to the patient and ventilator port of the manifold. The artificial airway maintenance system may be specifically adapted (e.g., sized and constructed) to facilitate safe and effective cleaning of artificial airways (e.g., endotracheal tubes) sized to be used in pediatric or neonatal patients (e.g., less than 7 mm in external diameter, less than 5 mm in external diameter, less than 4 mm in external diameter, less than 3 mm in external diameter, 2.5 mm or less in external diameter). In various embodiments, the modules are configured as closed system modules that include a flexible sheath configured to, during use, prevent exposure of a portion of the module and/or the artificial airway to an external environment.

The endotracheal tube cleaning module may include a catheter having an expandable cleaning member configured to wipe an interior surface of the artificial airway (e.g., endotracheal tube) to remove biofilm or other debris accumulated thereon. The expandable cleaning member may have a smooth, regular profile. In some embodiments, the expandable cleaning member comprises one or more rings, shavers or other wiper members. The rings, shavers or other wiper members may comprise one or more shearing or squared (or substantially squared) edges or may comprise a smooth contact surface with generally rounded edges. In various embodiments, the expandable cleaning member is pneumatically expandable or mechanically expandable. In some embodiments, at least one activation member is configured to compress a fluid or gas reservoir in fluid communication with the expandable cleaning member, thereby causing the expandable cleaning member to expand (e.g., inflate). The activation members may comprise plungers, syringes, buttons or other devices configured to be activated by a single actuation motion with a single press or touch of a finger. In some embodiments, upon expansion of the expandable cleaning member, at least a portion of the expandable cleaning member is configured to contact an interior surface of a body-inserted tube (e.g., endotracheal tube) such that, when the catheter is withdrawn from the body-inserted tube, biofilm (e.g., debris or secretions) collected on the interior surface is removed by the expandable cleaning member. The suction catheter cleaning device module includes a coupling member configured to couple to a suction port of a multi-port manifold or endotracheal tube adapter (e.g., dual-port or tri-port adapter). In one embodiment, the suction catheter cleaning device module includes a suction catheter configured to clean the interior surfaces of body-inserted tubes or artificial airways (alone or in addition to suctioning natural airways or portions of the respiratory tract or other body lumens).

The manifold or endotracheal tube coupling adapter may include multiple ports, such as a ventilator port, an instrumentation port and a distal port. The distal port may be configured to directly or indirectly (e.g., via a universal endotracheal tube connector) couple to an artificial airway (e.g., endotracheal tube). In some embodiments, the manifold or endotracheal tube adapter is transparent to facilitate viewing of markings (e.g., centimeter markings) on the catheters of the modules being inserted into the artificial airway through the manifold that are indicative of depth of insertion within the artificial airway (e.g., endotracheal tube), thereby preventing against over-insertion. The markings on the catheters may correspond to similar markings on the artificial airway (e.g., endotracheal tube).

In some embodiments, the expandable cleaning member of the endotracheal tube cleaning device includes a lubricant (e.g., a SURGILUBE lubricant) and/or a bactericide or antibacterial agent (e.g., chlorhexidine). The cleaning member alone, the catheter alone, or both the catheter and the cleaning member may be treated so that a bonded or integral lubricious coating (e.g., parylene) may facilitate insertion of the catheter and withdrawal of the catheter and deployed cleaning member. In one embodiment, the bactericide is activated by photodynamic means.

In accordance with several embodiments, a method for cleaning an endotracheal tube and/or distal airways (e.g., tracheobronchial tree) without removing a pediatric or neonatal patient from a ventilator is provided. In one embodiment, the method comprises coupling an endotracheal tube adapter or manifold to the endotracheal tube. In one embodiment, the endotracheal tube adapter or manifold comprises multiple ports, such as a distal coupling port, a ventilator port, and an access or instrumentation port. The method may further comprise removably connecting (e.g., via friction-fit engagement or mechanical interlocking engagement) a coupling member of a suction catheter system or module to the instrumentation port of the endotracheal tube adapter or manifold. In one embodiment, the suction catheter system or module includes a suction catheter and a flexible sheath configured to enclose the suction catheter when it is withdrawn from the endotracheal tube so as to provide a closed system.

The method further comprises coupling a ventilator to the ventilator port of the endotracheal tube adapter or manifold and inserting a distal end of the suction catheter through at least a portion of an endotracheal tube to perform suctioning of the endotracheal tube and/or portions of the tracheobronchial tree beyond the endotracheal tube. Ventilation may advantageously be maintained during performance of the entire method. In some embodiments, the manifold comprises a stopcock or other valve control adapted to open and close access to the endotracheal tube by the suction catheter and/or other instruments while still maintaining ventilation. The stopcock may include an occluder or barrier configured to seal off the manifold from exposure to the external environment or the flexible sleeve of a closed suction system module through the access or instrumentation port. An occluder may be toggled to an open configuration prior to insertion of the suction catheter. In one embodiment, the method includes decoupling the suction catheter cleaning module from the instrumentation port of the manifold. An occluder may be toggled to a closed or blocking configuration prior to removal of the suction catheter cleaning module so as to prevent air and positive ventilation pressure (e.g., positive end expiratory pressure) from leaking out of the manifold.

Either soon after removal of the suction catheter cleaning module (e.g., within a matter of seconds, 30 seconds to 5 minutes) or after a longer period of time (e.g., minutes to hours after), the method may further include removably coupling an endotracheal tube cleaning device module to the instrumentation port. The endotracheal tube cleaning device module includes a catheter having an expandable cleaning member positioned along a distal end portion of the catheter. The method may include advancing the catheter such that the expandable cleaning member is at or near a distal end of the endotracheal tube and then expanding the expandable cleaning member into an expanded configuration such that at least a portion of the expandable cleaning member is in contact with an interior surface of the endotracheal tube. The method may further include withdrawing the catheter from the endotracheal tube with the expandable cleaning member in the expanded configuration to effectively remove biofilm or debris that is accumulated on the interior surface of the endotracheal tube that may not have been suctioned out by the suction catheter (either because it was missed or because it is adhered in a manner that suctioning is not sufficient to remove it). The catheter may be removed from the endotracheal tube and out of the manifold into a cleaning chamber of the endotracheal tube cleaning device module. The endotracheal tube cleaning device module may include an irrigation port in communication with the cleaning chamber so as to facilitate irrigated cleaning of the cleaning member to facilitate reuse. An occluder may be toggled to a closed or blocking configuration after withdrawal of the catheter beyond the position of the occluder so as to prevent irrigation fluid from entering the artificial airway (and thus distal airways as well) and/or to prevent loss of positive ventilatory circuit pressure when the endotracheal tube cleaning device module is decoupled from the instrumentation port.

In some embodiments, the method comprises suctioning distal airways of a patient using the suction catheter. In one embodiment, the method comprises cleaning a distal tip of the suction catheter through an irrigation port either of the manifold or of the suction catheter cleaning module. In some embodiments, the method comprises collecting a portion of the removed biofilm for microbiologic evaluation. The method may comprise identifying a type of bacteria present within the removed biofilm (such as by polymerase chain reaction, infrared light detection, or other real-time or substantially real-time diagnostic or evaluation methods).

In accordance with several embodiments, a visualization device module configured to provide visualization of a patient's airways is provided. In one embodiment, the visualization device module includes a distal coupling member configured to couple to the instrumentation port of the manifold. In one embodiment, the visualization device module includes a visualization device (e.g., bronchoscope) sized and configured to extend from a mouth of a patient to distal portions of the respiratory tree of a patient. In one embodiment, the visualization device module includes a flexible sleeve coupled to the distal coupling member and extending proximally therefrom to enclose the visualization device when the visualization device is outside of the patient, thereby isolating the visualization device from exposure to outside air or external contamination. In one embodiment, the visualization device (e.g., flexible fiber optic scope) may be introduced via an angled irrigation port of a closed system manifold including a seal or mechanical coupling. In some embodiments, the visualization device includes a suction lumen, a visualization lumen, and/or an irrigation lumen. Any of the modules described above may be interchangeably coupled to the manifold multiple times without disconnecting the patient from the ventilator and without loss of positive ventilatory circuit pressure through the manifold because of the rotatable occluder.

In some embodiments, the suction catheter has an outer diameter that is less than 70% (e.g., 20%, 25%, 30%, 35%, 40%, 45%, 50%, 55%, 60%, 65%) of the inner diameter of the body-inserted tube (e.g., endotracheal tube, chest drainage tube, urinary catheter). The outer cross-sectional dimension of the suction catheter may be sized such that the suction catheter does not significantly compromise airflow during its insertion, or during suctioning and removal. In one embodiment, the outer diameter of the suction catheter is less than 50% of the inner diameter of the body-inserted tube. In one embodiment, the outer diameter of the suction catheter is no larger than 70% of the diameter of the lumen of the body-inserted tube.

According to some embodiments, a kit (e.g., system or collection of items for a common purpose) for removing biofilm (e.g., debris) that has collected within one or more airways (e.g., native airway, oral cavity, nasal passages, pharynx, larynx, trachea, and/or any portion of the lungs, including any of the branches of the tracheobronchial tree, endotracheal tube, etc.) of a patient is provided. The tem "kit" as used herein should be given its ordinary meaning and should include any system, grouping and/or collection of devices, systems, modules, components, features, materials and/or the like provided for a common goal. In one embodiment, the kit includes one or more of the following, depending on the needs or clinical situations handled by the patient care facility: an artificial airway (e.g., endotracheal tube or other body-inserted tube), an endotracheal tube cleaning device or module, a suction catheter or cleaning module, a visualization device or module (e.g., bronchoscope), a multi-port manifold or endotracheal tube adapter, accessory caps, and/or any other system, device or component. The kit can further comprise instructions for using the various devices, components and/or other features of the kit for a particular cleaning protocol or procedure. For example, such instructions for use can include details regarding the order in which the devices, systems or other components are used, the duration of use and/or the like.

In some embodiments, one or more ports of the adapters or manifolds described herein can be shaped, angled or curved in a similar manner as the device being introduced through the port to aid in the ease of introduction, removal and collection of organized secretions or biofilm. The adapters or manifolds can be connected to any tube-like structure, including, but not limited to, endotracheal tubes, percutaneous tracheostomy devices, urinary catheters, or dialysis catheters, chest tubes, or other catheters and tubes.

In accordance with some embodiments of the invention, the adapters or manifolds can be used with "closed suction" systems. The adapter or manifold can include three ports, with one port or tube for connection to oxygen tubing or directly to a ventilator, one port or tube for instrumentation access, and one port to connect to an artificial airway (e.g., endotracheal tube). The ventilator port and the instrumentation access port may form a Y connection to the distal port. The occluder may be positioned just proximal to the intersection of the two ports forming the Y so as to advantageously reduce or minimize the amount of ventilatory dead space within the manifold. The manifold can be configured to be used multiple times or a single time. Any ports or tubes not in use can be sealed and capped.

In some embodiments, the suction catheter cleaning module and/or the endotracheal tube cleaning device module includes a polymeric tubular extension or proboscis coupled to the manifold and extending into the flexible enclosure, wherein the tubular extension is configured to receive a flexible catheter and pull the flexible catheter at least partially into the body-inserted tube through the manifold. The polymeric tubular extension may be particularly advantageous for soft, pliable catheters or instruments and/or catheters having outer diameters of less than 5 mm (e.g., catheters designed for neonate or pediatric patients).

According to some embodiments, the devices and/or systems disclosed herein are advantageously disposable and relatively inexpensive to manufacture. Thus, such embodiments do not require subsequent cleaning, sterilization, and repackaging. Some embodiments are advantageous because they can be performed via the natural airway of a patient while a patient undergoes assisted ventilation utilizing an endotracheal or tracheostomy tube.

In several embodiments, the cleaning device is particularly advantageous because it rejuvenates endotracheal tubes that have been clogged or otherwise contaminated with biofilm. In one embodiment, the cleaning device removes biofilm such that endotracheal tube resistance is decreased by at least 20% after cleaning, thus enhancing the functionality of the endotracheal tube. In some embodiments, the cleaning device removes greater than 99% of bacteria (as determined by colony counts in the biofilm) from the endotracheal tube. Thus, in several embodiments, the cleaning device offers significant economic and clinical benefits. Some embodiments disclosed herein are particularly advantageous because they do not require performance by a physician and do not require sedation, short acting paralytics, increased intravenous fluid administration, and/or vasopressors. Some embodiments of the inventions are advantageous because they are minimally invasive and they minimize pain and discomfort to the patient and minimize the overall time of cleaning. Some embodiments of the inventions reduce the number of times that suctioning must be performed in a twenty-four hour period.

In accordance with several embodiments, a system for maintenance of an artificial airway (e.g., endotracheal tube) having an external diameter of less than 5 mm (e.g., less than 5 mm, less than 4 mm, less than 3 mm, 2.5 mm or less) includes a multi-port manifold or adapter. The manifold includes two proximal ports and one distal port. The proximal ports include a ventilation port configured to be removably coupled to a ventilator and an access port configured to be removably coupled to multiple modules adapted to access and/or treat the artificial airway (e.g., endotracheal tube) through the manifold. The distal port is configured to be removably coupled to the artificial airway (e.g., via friction-fit, mechanical interlock or other engagement mechanism). The ventilation port and the access port branch off from a main body of the manifold to form a Y shape. The manifold further includes an occluder (e.g., stopcock or valve) positioned at or near a location along a length of the manifold at which the ventilation port and the access port branch off from the main body of the manifold. The occluder is configured to transition between an open configuration and a closed configuration. In the closed configuration, a lumen of the manifold in communication with the distal port and a lumen of the ventilator port are sealed off from a lumen of the access port. In this embodiment, the occluder includes an external knob and an internal barrier (e.g., sealing member) extending laterally from the external knob. The internal barrier of the occluder is shaped and sized so as to effectively seal off the access port from the remainder of the manifold (e.g., the distal port and the ventilator port) when the occluder is in the closed configuration, thereby reducing an amount of dead space of a ventilatory circuit within the manifold. The barrier or sealing member may be substantially planar so as not to interfere with introduction of instruments when the occluder is in the open configuration. In some embodiments, the knob is configured to be rotated 90 degrees to transition between the open configuration and the closed configuration.

The system may further include a suction catheter module configured to be removably coupled to the access port of the manifold. The suction catheter module includes a suction catheter configured to be introduced into the artificial airway (e.g., endotracheal tube) through the manifold and to suction out accumulated biofilm from the artificial airway and/or portions of a tracheobronchial tree distal to the artificial airway. The system may also include an artificial airway cleaning device module (e.g., endotracheal tube cleaning device module) configured to be removably coupled to the access port of the manifold. The artificial airway cleaning device module includes a flexible catheter having a distal expandable cleaning member, the flexible catheter being configured to be introduced through the manifold into the artificial airway. The distal expandable member is configured to be expanded into contact with an interior surface of the artificial airway (e.g., endotracheal tube). The flexible catheter is configured to be withdrawn from the artificial airway with the distal expandable member in an expanded configuration to remove additional biofilm (e.g., the more dense secretions or the secretions that are more tightly adhered to the surface of the artificial airway) from the artificial airway. The artificial airway may be an endotracheal tube designed for insertion within pediatric and/or neonatal patients and may have an external diameter of less than 7 mm, less than 5 mm, less than 4 mm, less than 3 mm, 2.5 mm or less).

In some embodiments, the artificial airway cleaning device module includes a syringe configured to transition the distal expandable cleaning member from an unexpanded configuration to the expanded configuration. The flexible catheter of the artificial airway cleaning device module includes a pilot channel extending from the syringe to the distal expandable cleaning member. The syringe may be adapted to provide a fixed volume of air sufficient to inflate the expandable cleaning member into the expanded configuration. The fixed volume of air may be a predetermined amount based on the diameter of the artificial airway (e.g., endotracheal tube) into which the artificial airway cleaning device is designed to be inserted. For example, a chamber of the syringe may include a pre-drilled hole positioned at a location along the chamber of the syringe so as to provide the fixed volume of air, thereby providing controlled expansion and avoiding overexpansion of the expandable cleaning member.

In some embodiments, the suction catheter module includes a flexible sheath extending from a proximal portion of the suction catheter module to a distal connector configured to couple to the access port of the manifold so as to provide a closed suction system. The artificial airway cleaning device module may include a flexible sheath extending from a proximal connector to a distal connector configured to couple to the access port of the manifold so as to provide a closed system.

In some embodiments, the artificial airway cleaning device module includes a conical extension member (e.g., proboscis) extending from the distal connector to a location along a length of the catheter, wherein an outer cross-sectional dimension of the conical extension member decreases from a distal end of the extension member to a proximal end of the extension member, and wherein the conical extension member is configured to facilitate entry of the flexible catheter into the manifold and gathering of the flexible sheath such that the flexible sheath does not substantially interfere with advancement of the flexible catheter into the manifold. The artificial airway cleaning device module may include an irrigation port configured to facilitate introduction of irrigating fluid to clean the expandable cleaning member after the catheter is removed from the manifold.

In accordance with several embodiments, a method of cleaning an endotracheal tube inserted within a body of a pediatric or neonatal patient without disconnecting the patient from a ventilator and without removing the endotracheal tube from the body is disclosed. The method includes coupling a distal port of a multi-port manifold to an endotracheal tube having an external diameter of less than 5 mm (e.g., less than 5 mm, less than 4 mm, less than 3 mm, 2.5 mm or less). The method also includes coupling a first proximal port of the manifold to a ventilation source (e.g., ventilator or ventilation unit). The method further includes reversibly coupling (e.g., via friction-fit, mechanical interlocking or other engagement mechanism) a suction catheter cleaning module to a second proximal port of the manifold, the suction catheter cleaning module including a suction catheter sized to fit within the endotracheal tube. The method includes advancing a distal end of the suction catheter through the distal port of the manifold and into the endotracheal tube and activating a suction source so as to facilitate removal of biofilm from the endotracheal tube through one or more suction ports at the distal end of the suction catheter. The method may optionally include advancing the distal end of the suction catheter beyond an open distal end of the endotracheal tube to suction distal airways (e.g., portions of the tracheobronchial tree). The method further includes decoupling the suction catheter cleaning module from the second proximal port of the manifold.

The method may further include reversibly coupling (e.g., via friction-fit, mechanical interlocking or other engagement mechanism) an endotracheal tube cleaning module to the second proximal port of the manifold. The endotracheal tube cleaning module includes a flexible catheter having an expandable cleaning member positioned along a distal end portion of the flexible catheter. The method may also include performing a cleaning procedure within the endotracheal tube by expanding the expandable cleaning member into an expanded configuration such that at least a portion of the expandable cleaning member is in contact with an interior surface of the endotracheal tube and then withdrawing the flexible catheter proximally out of the endotracheal tube with the expandable cleaning member in the expanded configuration. The endotracheal tube cleaning module may be decoupled from the second proximal port of the manifold after performing the cleaning procedure.

In some embodiments, the method includes introducing fluid through an irrigation port of the endotracheal tube cleaning module to clean the expandable cleaning member after decoupling the endotracheal tube cleaning module from the second proximal port of the manifold. The method may also include enabling access to the distal port of the manifold and the endotracheal tube by causing an occluder of the manifold to transition to an open configuration from a closed configuration prior to the step of advancing a distal end of the suction catheter through the distal port of the manifold and into the endotracheal tube, thereby providing unobstructed access through the manifold. The method may further include occluding the manifold so as to prevent loss of positive end expiratory pressure in a ventilatory circuit due to dead space in the manifold proximal to a Y junction formed by the first proximal port and the second proximal port.

In accordance with several embodiments, a connector interface includes a distally-tapered outside end and a proximally-tapered conical inside end for collection and retention of debris removed from a tube by a catheter or other instrument inserted through the connector interface. The connector interface may also include a side port positioned along a length of the connector interface between a proximal end and a distal end of the connector interface that is adapted for providing irrigation cleaning of the catheter or instrument.

In accordance with several embodiments, a sterilization device adapted to removably couple (e.g., via friction-fit, mechanical interlocking or other engagement mechanism) to a catheter or other device (e.g., a suction catheter of a suction catheter device module, a suction catheter device module, a catheter of an artificial airway cleaning device module, an endotracheal tube cleaning module, a visualization device module). The sterilization device includes a proximal end having an ultraviolet-C (UV-C) light source and a coupling mechanism adapted to removably couple (e.g., via friction-fit, mechanical interlocking or other engagement mechanism) to the catheter or other device. The sterilization device includes a power switch adapted to prevent light emission when the sterilization device is not coupled to the catheter or other device. The sterilization device may also include an integrated timer configured to ensure proper duration of light emission by the UV-C light source. The sterilization device may further include an indicator light adapted to indicate when the sterilization device is active and/or when a light delivery cycle is complete. In embodiments incorporating rechargeable power sources, the sterilization device can include a recharging interface adapted to recharge the one or more rechargeable power sources. In one embodiment, the sterilization device includes a low power indicator. In one embodiment, the sterilization device includes quartz protuberances adapted to transmit UV-C light deeper into a cleaning chamber of the catheter or other device.

For purposes of summarizing the disclosure, certain aspects, advantages and novel features of embodiments of the inventions have been described herein. It is to be understood that not necessarily all such advantages can be achieved in accordance with any particular embodiment of the inventions disclosed herein. Thus, the embodiments disclosed herein can be embodied or carried out in a manner that achieves or optimizes one advantage or group of advantages as taught herein without necessarily achieving other advantages as can be taught or suggested herein. The methods summarized above and set forth in further detail below describe certain actions taken by a practitioner; however, it should be understood that they can also include the instruction of those actions by another party. Thus, actions such as "inserting a suction catheter" include "instructing the insertion of a suction catheter." Further aspects of embodiments of the invention will be discussed in the following portions of the specification. With respect to the drawings, elements from one figure may be combined with elements from the other figures.

BRIEF DESCRIPTION OF THE DRAWINGS

FIGS. 3A and 3B illustrate a portion of an embodiment of a catheter shaft of the cleaning device module of FIG. 2 that includes a coextruded material (before and after a curing process, respectively).

FIG. 5 illustrates an embodiment of a sterilization cap. FIG. 5A illustrates an embodiment of a window within the sterilization cap of FIG. 5.

FIGS. 10A and 10B illustrate one embodiment of a distal portion of a suction catheter device comprising an expandable cleaning portion.

FIGS. 11A-11C illustrates various views of an embodiment of a suction catheter device comprising an expandable cleaning portion positioned within an interior of an endotracheal tube or other body inserted tube.

DETAILED DESCRIPTION

Figure 1:
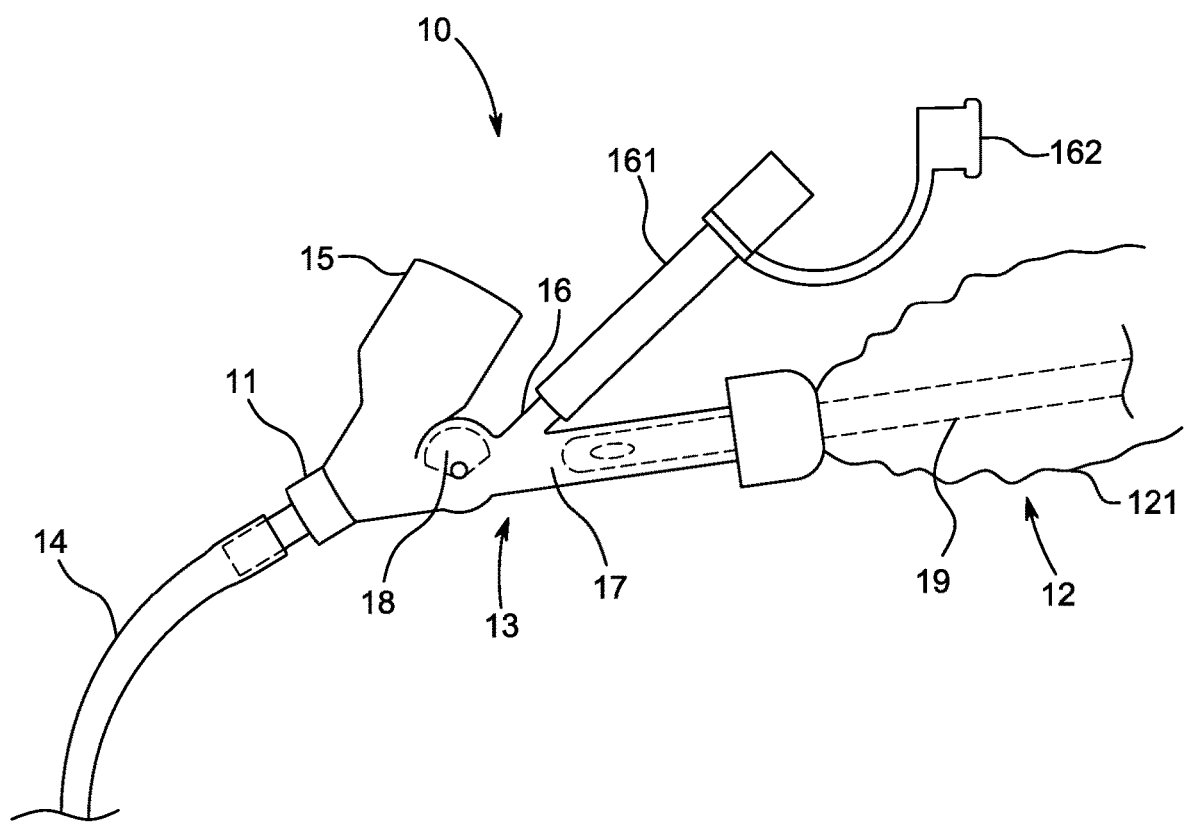
FIG. 1 illustrates one embodiment of a pediatric and/or neonatal airway management system.

Several embodiments of cleaning systems, devices and methods described herein are particularly well-suited to remove biofilm (e.g., secretions, debris and/or other materials) from body-inserted tubes (e.g., endotracheal tubes) and the respiratory tract or tree of a patient within a closed or partially closed suction system while a patient is connected to a ventilator The various devices, systems, methods and other features of the embodiments disclosed herein may also be utilized or applied to other types of apparatuses, systems, procedures, and/or methods, whether medically related or not. For example, the embodiments disclosed herein can be utilized for, but are not limited to, bronchoscopes, chest drainage tubes, gastrostomy drainage tubes, abdominal drainage tubes, other body drainage tubes, feeding tubes, endoscopes, percutaneous dialysis catheters, urinary catheters, urethral catheters, Foley catheters, and any other percutaneous or per os catheters or body-inserted tubes.

The materials used for the various components of the cleaning and/or visualization devices and systems described herein can advantageously comprise one or more biocompatible materials. Such materials can be rigid or semi-rigid and/or flexible, as desired or required for a particular application or use. The materials used can include, but are not limited to, polyether ether ketone (PEEK), Nylon 6/6, polyethylene, polypropylene, polyethylene terephthalate (PET), glycol-modified PET, polyvinyl chloride (PVC), thermoplastic elastomers (TPEs) such as PEBAX TPEs, other natural or synthetic polymers (e.g., KRATON polymers), silicone, natural rubber, latex, polycarbonate, K resin, acrylonitrile butadiene styrene (ABS), styrenes and/or other thermoplastic elastomers or polymers.

The terms "debris" and "secretions" as used herein shall be given their ordinary meaning and shall include, without limitation, biological fluids, solids, gels, deposits, films, debris, and/or secretions, such as mucosal secretions, blood, bacteria, biofilm, viruses, other microorganisms, protein, feces, urine, albumin and/or any other biological or biologically-related materials. The term "native airway(s)" as used herein shall be given its ordinary meaning and shall include, without limitation, the oral cavity, nasal passages, pharynx, larynx, trachea, and/or any portion of the lungs, including any of the branches of the tracheobronchial tree.

The term "biofilm" as used herein shall be given its ordinary meaning and shall include, without limitation, biological fluids, solids, gels, deposits, films, debris, and/or secretions, such as mucosal secretions, blood, blood clots, bacteria, viruses, other microorganisms, protein, feces, urine, albumin and/or any other biological or biologically-related materials. In some embodiments, the biofilm may comprise any debris that can be deposited and come to rest within a lumen of an endotracheal tube, such as blood clot material, mucus, secretions, biofilm, or any other type of particulate matter that might find itself within the lumen of an endotracheal tube. In some embodiments, the biofilm may comprise any debris collected or removed from native airways of a patient or from a body-inserted tube.

Conventional closed suction catheter cleaning and optimal humidification does not adequately keep endotracheal tubes free of accumulated secretions or microbial colonization and biofilm formation. While this accumulation of secretions in larger adult-sized endotracheal tubes is clinically significant and requires removal for best patient outcome, even the smallest bit of retained secretions in pediatric and neonatal sized endotracheal tubes (e.g. tubes having an inner diameter of less than 7 mm or between 2.0 and 6.5 mm) imposes a critical restriction in airflow and much increased work of breathing. This is because resistance to airflow in a tube is inversely proportional to the radius of the tube to the fourth power, as expressed in Pouseille's equation:

$$R = \frac{8nL}{\pi r^4}$$

Smaller tubes have very high resistance to begin with, and any residual obstruction may contribute to ongoing respiratory failure in the child or neonate. It is also well appreciated that retained secretions and microbial colonization result in biofilm formation within essentially all endotracheal tubes over time, that biofilm is at least part of the pathophysiology of ventilator associated pneumonia, and that every effort should be made to eliminate its development within the endotracheal tube or other body-inserted tube.

Due to the limitation in suction negative pressure that can be applied (e.g., 80 cm $H_2O$), the small size of suction catheters themselves, and the need to keep the suction catheters smaller than the internal diameter of the endotracheal tube, suctioning alone invariably leaves some secretions and debris behind in endotracheal tubes sized and configured for pediatric or neonatal patients (e.g., pediatric and neonatal-sized tubes having an internal diameter of less than 7 mm, such as between 2.0 and 6.5 mm). In order to try and clear the pediatric or neonatal-sized tube better, practitioners sometimes use suction catheters larger than recommended to try to "bulldoze" a clearer path because they do not want to have to exchange the endotracheal tube. As a last resort, but entirely too often, endotracheal tubes have to be exchanged, which can result in severe adverse consequences to the patient, including death. What is needed is a device that can safely, efficiently, and effectively remove the retained secretions and debris that standard suction (open or closed) systems leave behind and to be able to do so in even the smallest of endotracheal tubes (e.g., pediatric and neonatal-sized tubes having an internal diameter of less than 7 mm, such as between 2.0 and 6.5 mm).

FIG. 1 illustrates one embodiment of a pediatric and neonatal-sized airway management, or maintenance, system 10. The illustrated system 10 is a closed suction system; however, at least some of the components could be used in a non-closed or open suction environment in alternative embodiments. In various embodiments, the pediatric and neonatal-sized airway management system 10 allows for, or facilitates, suctioning, endotracheal tube cleaning, administration of fluids and/or light, visualization of the endotracheal tube and distal airways, and/or introduction of other instrumentation, as desired and/or required. Pediatric and neonatal suction systems (whether open or closed) may require transient removal to effectively clean the smallest (about 2.0 mm and up) ET tubes. In accordance with several embodiments, the pediatric and neonatal-sized airway management system 10 facilitates cleaning using an endotracheal tube cleaning device sized to fit within a pediatric and neonatal-sized endotracheal tube without breaking the ventilatory circuit, thereby reducing the likelihood of hypoxemia, loss of tidal volume, loss of positive end-expiratory pressure (PEEP), and derecruitment of the lung alveoli.

The system 10 includes a closed suction cleaning device module 12 and a manifold 13. A distal port of the manifold 13 is illustrated as being coupled to an endotracheal tube 14. Endotracheal tubes typically vary in size between about 2.0 mm internal diameter and 9.0 mm internal diameter. Pediatric and neonatal-sized tubes typically have an internal diameter of less than 7 mm, such as between 2.0 and 6.5 mm. The distal port 11 of the manifold (e.g., a variable size connector) can be sized as appropriate to match the internal diameter of the endotracheal tube 14 to which it is being connected. The distal port 11 reversibly couples to the manifold 13 and is chosen from a variety of available sizes to accommodate endotracheal tubes of various diameters. In one embodiment, the distal port 11 is coupled to the endotracheal tube 14 using a universal endotracheal tube connector (e.g., via friction-fit coupling). The manifold 13 also includes a standard size ventilator connection port 15. The illustrated embodiment of the manifold 13 also includes two additional ports, a flush port 16 and a main instrumentation port 17. The main instrumentation port 17 is illustrated as being in-line with the distal port 11 but may be arranged at an angle in other embodiments. As shown, the closed suction cleaning device module 12 is removably coupled (e.g., via friction-fit coupling or mechanical interlocking coupling mechanisms) to the instrumentation port 17 and includes a sleeve, or sheath, 121 to prevent against contamination. The closed suction cleaning device 12 and the manifold 13 may incorporate any of the structural or functional features of the corresponding devices or components (e.g., closed suction devices 3200, 3300, 3400, 3500 and manifolds 3010, 4830, 5030, 5232) described and/or illustrated in PCT Publication No. WO 2015/187583 or described and/or illustrated herein. The sleeve, or sheath, 121 may incorporate any of the structural or functional features of the corresponding components (e.g., sleeve 3090) described and/or illustrated in PCT Publication No. WO 2015/187583 or described and/or illustrated herein. The system may also be adapted for adult-sized systems.

The manifold 13 includes a manifold occluder 18 (e.g., stopcock, shutoff member, barrier) adapted to occlude the manifold 13 (e.g., block air flow from the ventilator port 15 to the instrumentation port 17 or flush port 16 and/or block insertion of instrumentation into the endotracheal tube 14 through the distal port 11) in a closed configuration. As shown, the manifold occluder 18 is positioned immediately adjacent to the ventilator connection port 15. The manifold occluder 18 is shown in the open position, or configuration. When the manifold occluder 18 is in the open configuration, a closed suction catheter 19 of the closed suction cleaning device module 12, an endotracheal tube cleaning device (e.g., catheter), or other catheters, scopes, or instruments can be inserted into the endotracheal tube 14 through the manifold 13 (e.g., in through instrumentation port 17 and out through distal port 11). When the manifold occluder 18 is toggled (e.g., rotated) to the closed position, or configuration, no catheters or other instruments can pass into the endotracheal tube 14 through the manifold 13.

Figure 6A:
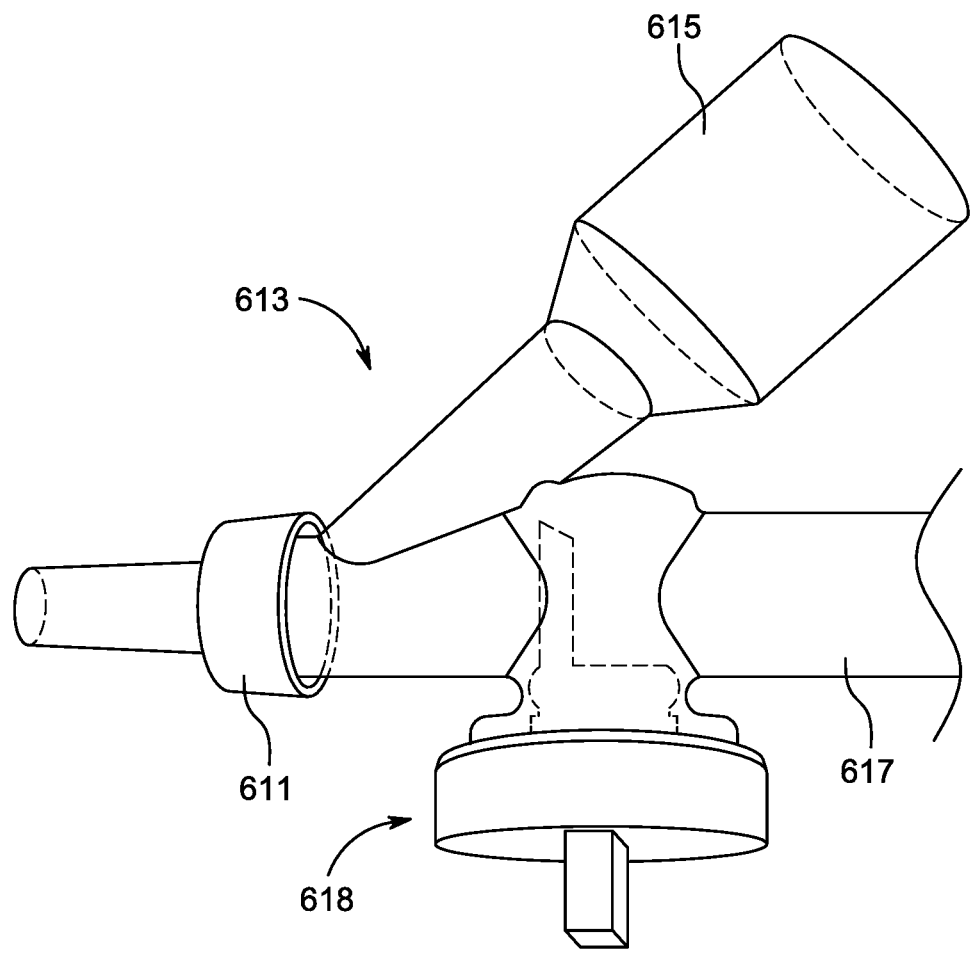
FIG. 6A illustrates a perspective view of an embodiment of the manifold with the access port lumen closed.
Figure 6B:
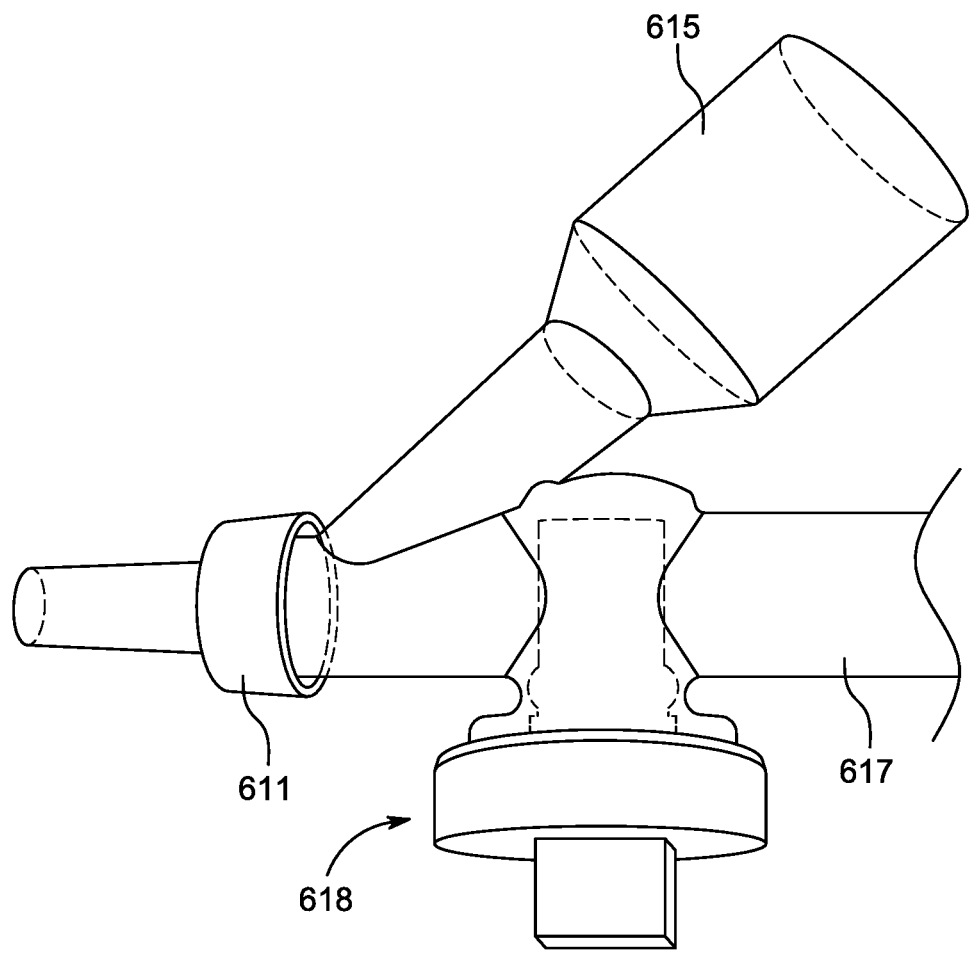
FIG. 6B illustrates a perspective view of the embodiment of the manifold of FIG. 6 with the access port lumen opened.

FIGS. 6A and 6B illustrate an embodiment of a manifold 613 (which may be similar to manifold 13 or replace manifold 13 in system 10) in a closed configuration and an open configuration, respectively. In use, according to some embodiments, a suction catheter, an endotracheal tube cleaning device, a visualization device and/or other device or instrument is advanced through an instrumentation access port 617 of the manifold 613 and out the distal port 611 connected to an artificial airway (e.g., endotracheal tube) or other body-inserted tube while the occluder is in an open configuration (as shown in FIG. 6B). After the cleaning and/or diagnostic procedure is performed using the suction catheter, endotracheal tube cleaning device, visualization device and/or other device or instrument, the device or instrument can be withdrawn rearwardly or cephalad through the manifold 613 such that the distal tip of such device or instrument resides just proximally to the occluder 618, which may then be closed by rotating a handle or knob 614 of the occluder 90° to the closed configuration (as shown in FIG. 6A). As shown in FIGS. 6A and 6B, the manifold occluder 618 may include a barrier or sealing member 619 coupled to the handle or knob 614 such that rotation of the handle or knob 614 causes rotation of the barrier or sealing member 619. The barrier or sealing member 619 may be sized and shaped so as to match a shape of the inner curved surface of the manifold 613 so as to effectively seal off the portion of the manifold 613 proximal to the barrier or sealing member 619 from fluid penetration or pressure loss or leakage when the barrier or sealing member 619 is in the closed configuration and so as not to hinder insertion of instruments through the manifold when the barrier or sealing member 619 is in the open configuration. The manifold occluder 18 described herein may incorporate the structural and functional features of the occluder 618 or may be substituted with the occluder 618 as illustrated in FIGS. 6A and 6B.

The manifold occluder 18, 618 and its positioning advantageously reduces (e.g., minimizes) the ventilation dead space in the manifold 13, 613 and thus, in the ventilatory circuit. In accordance with several embodiments, by designing the manifold occluder 18, 618 (e.g., stopcock, shutoff member or valve, barrier) in such a manner that it rotates toward the patient, the dead space can advantageously be reduced to the absolute minimum required and would be as if there were only a ventilator connection present and not another branch or port forming a "Y", which other branch or port leads to a catheter interface, thereby reducing or eliminating unnecessary dead space, and thereby improving the efficiency of the breathing or ventilatory circuit. In the intubated neonate, physiologic dead space is the sum of the breathing apparatus, the airways, and any non-perfused alveoli. Neonates are particularly sensitive to the impact of breathing apparatus volume added to the ventilatory circuit, as even small increases in apparatus dead space can significantly increase $PCO_2$ or the minute ventilation needed to maintain a normal $PCO_2$. This dead space issue applies to the Y connection of the manifold to the endotracheal tube as well as other more proximal parts of the ventilatory circuit. For neonates with small lung capacity, any resistance, turbulence or breathing inefficiency that can be eliminated or reduced is helpful to the patient, and can advantageously prevent the clinician from having to increase ventilation pressures to try to accommodate for losses due to dead space in the manifold (e.g., manifold 13, 213, 613). The manifold occluder 18 may comprise a stopcock mechanism or other suitable shut-off mechanism (e.g., positive, continuous, physical barrier) adapted to have a closed configuration in which the passageway is blocked and an open configuration in which the passageway is open.

Figure 7:
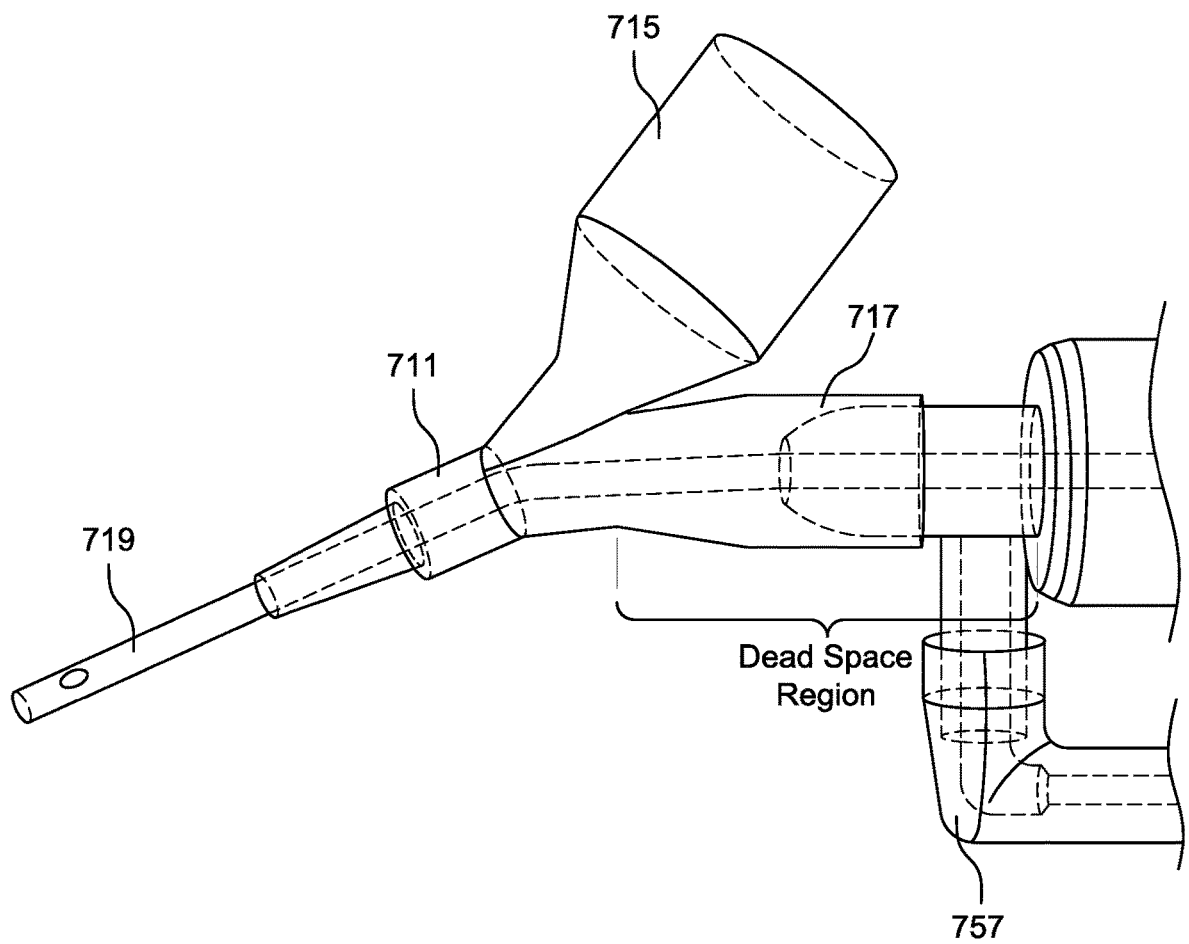
FIG. 7 illustrates a prior art manifold having dead space from at least the intersection of the "Y" branches with the main body of the manifold to the catheter irrigation connection.
Figure 8:
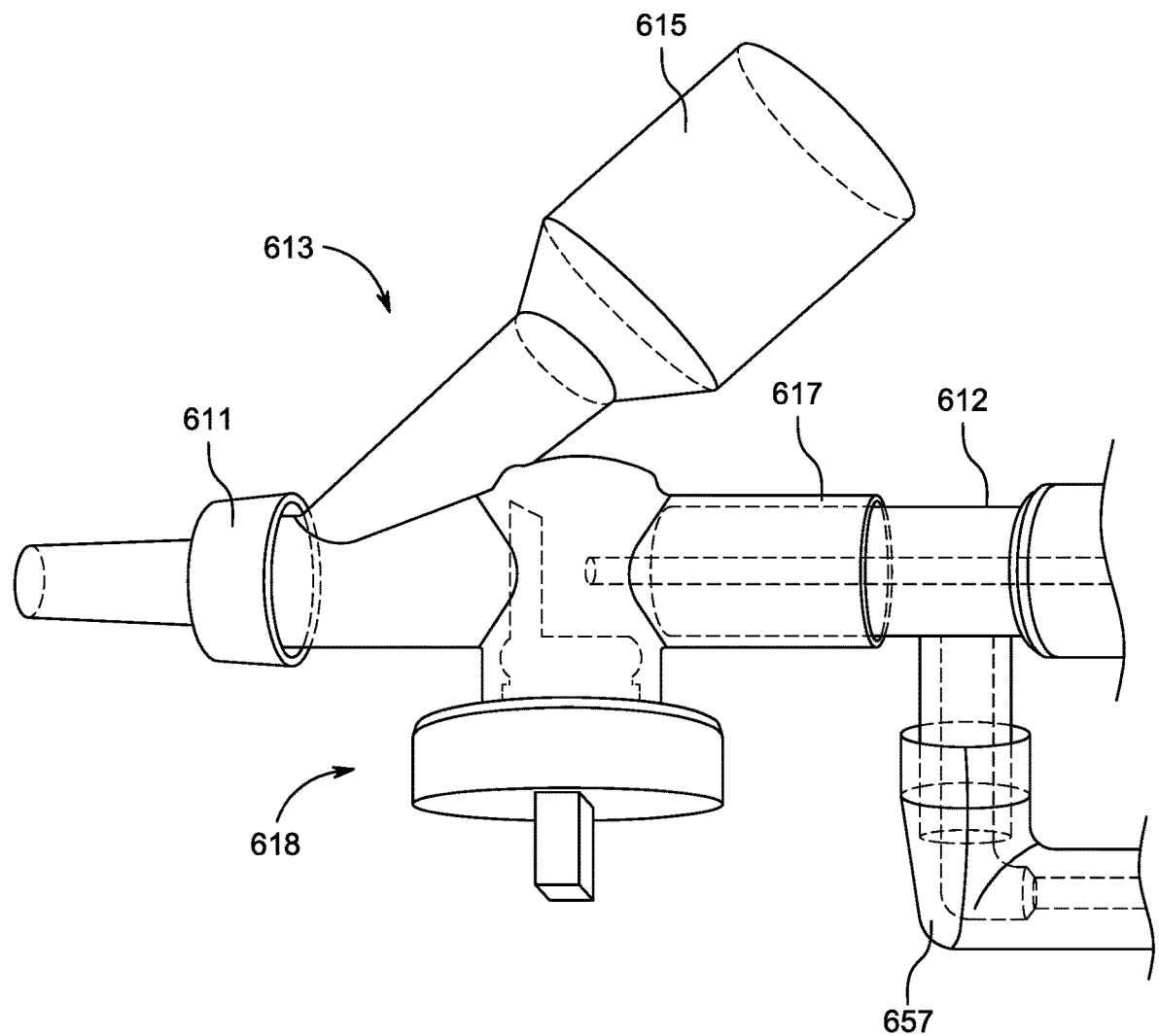
FIG. 8 illustrates an embodiment of the manifold of FIGS. 6A and 6B coupled with a suction catheter module and shows that the dead space has been eliminated proximal of the intersection of the "Y" branches with the main body of the manifold.

Elevated tidal volume, minute ventilation, and peak inspiratory pressure correlates directly with the severity of broncho-pulmonary dysplasia in preterm infants. Therefore, current approaches to lung protective ventilation mandate that tidal volume and respiratory rate be limited to minimize the risk of ventilator-induced injury. When employing a lung protective ventilation strategy, apparatus dead space, including the dead space in the manifold (e.g., Y connector) should be minimized to avoid unnecessary hypercarbia or excessive minute ventilation, in accordance with several embodiments. FIG. 7 illustrates a conventional prior art manifold 713 having a distal port 711 and two proximal ports 715, 717 that form "Y" branches. As shown in FIG. 7, the conventional prior art manifold 713 has a dead space region extending from at least the intersection of the "Y" branches 715, 717 with the main body of the manifold 713 to the irrigation port 757 of the suction catheter module 712 including a suction catheter 719. As shown in FIG. 8, the manifolds disclosed herein (e.g., manifold 13, 213, 613) advantageously allow for a positive close off of potential dead space in the Y connector proximal to the intersection of the two branches (e.g., ventilation port 615 and access port 617) of the Y, thereby helping to minimize the required tidal volume and minute ventilation of intubated neonates in order to maintain normal $PCO_2$. The design of the close-off feature 618 (e.g., stopcock or solid, physical barrier or occluder that can be rotated in and out of its occlusive or blocking configuration) allows predictable isolation of the access port 617 of the manifold (e.g., manifold 13, 213, 613) from the ventilatory circuit and the distal port 611, minimizes dead space within the Y connector portion of the manifold (e.g., manifold 13, 213, 613) as much as possible, and is small and light. In addition, the positive close off feature 618 of the manifold, as opposed to a "diaphragm valve" or "trap door", allows cleaning of devices without saline aspiration, and removal and reconnection of multiple devices from the manifold (e.g., manifold 13, 213, 613) without interrupting the patient/ventilatory circuit. This preserves tidal volume and positive end expiratory pressure and prevents alveolar derecruitment, and can also advantageously reduce the likelihood of clinicians increasing ventilator pressures to account for loss of positive pressure due to dead space.

Referring back to FIG. 1, also when in the closed configuration, saline or other solutions (antimicrobials, etc.) can be introduced through the flush port 16 and suctioned into the closed suction catheter 19. Valves at the proximal portion of a flush port 16 or a connection member 161 coupled to the flush port 16 and/or the distal portion of the closed suction catheter 19 enclosure may advantageously prevent loss of tidal volume, airway pressure, or PEEP when endotracheal tube cleaning, instrumentation, or closed suctioning is being performed. The valved flush connection member 161 or flush port 16 can be used to introduce or infuse saline or other solutions such as anti-microbials into the closed suction cleaning device module 12 or the Y connector portion of the manifold 13.

Figure 1A:
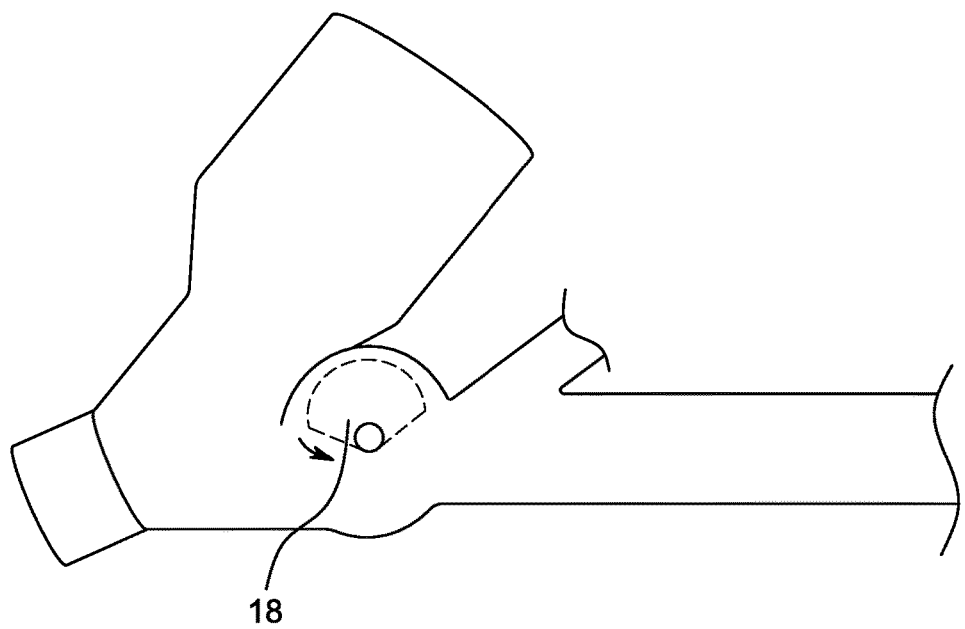
FIG. 1A illustrates a close-up view of a portion of a manifold, or connector, of the airway management system of FIG. 1.
Figure 2:
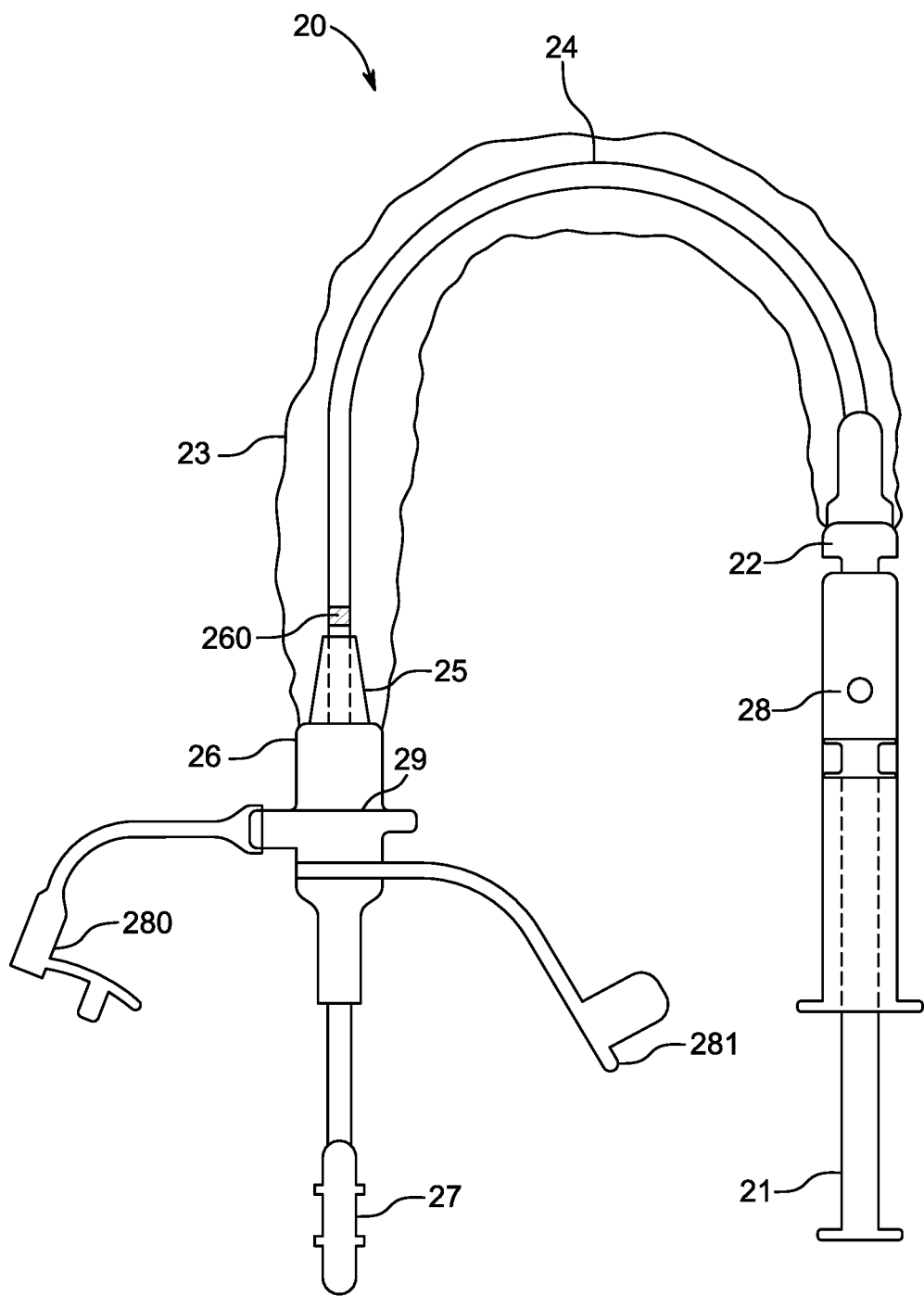
FIG. 2 illustrates an embodiment of an endotracheal tube cleaning device module.

The main instrumentation port 17 or the valved flush connection or flush port 16 can also be used to insert an endotracheal tube cleaning catheter (e.g., a catheter having an external diameter of about 2.0 mm with one or more expandable cleaning members positioned along an outer surface of the catheter such as shown in FIG. 2), a visualizing scope (e.g., a scope having an external diameter of about 2.0 mm), or another catheter for introduction of irrigation, light therapy, or other therapeutics to the distal lung fields (such as surfactant to treat immature lungs). Once any of these catheters or instruments are withdrawn, the manifold 13 can be closed off by rotating the occluder 18 in the direction of the illustrated arrow in the close-up view of FIG. 1A, the catheter or instrument can be completely withdrawn from the flush port 16 or main instrumentation port 17, and the space proximal to the site of the distal manifold closure (e.g., the occluder 18) can be irrigated and cleaned with the irrigant being suctioned into the closed suction catheter 19. The catheter or instrument (e.g., endotracheal tube cleaning catheter) can be flushed, capped and/or discarded as appropriate per their instructions for use. The flush port 16 may also be capped with a cap 162 (tethered or untethered) when not in use. In some embodiments, the flush port 16 is not a port of the manifold 13 and the manifold 13 just has the ventilator port 15 and the main instrumentation port 17 to form a single Y with the distal port forming the bottom of the Y. The flush port 16 instead may be a component of the closed suction cleaning device module 12 (as shown, for example, in FIGS. 2B and 8).

In some embodiments, an endotracheal tube cleaning device (e.g., module) is transiently exchanged for the closed suction catheter module 12 or the suction catheter 19 through the main instrumentation port 17, the endotracheal tube 14 then being effectively cleaned, and the endotracheal tube cleaning device (e.g., module) is then removed from the manifold 13 and stored off-line (e.g., no longer coupled to the manifold 13) and the closed suction cleaning device module 12 reconnected to the endotracheal tube 14 (e.g., via the instrumentation port 17 of the manifold 13). In other embodiments, an endotracheal tube cleaning device is inserted into a side port (e.g., flush port 16) of the manifold 13, the endotracheal tube is then effectively cleaned, and the endotracheal tube cleaning device is then withdrawn from the manifold 13, all without breaking the ventilatory circuit (and therefore always maintaining desired tidal volume, pressure, and PEEP (alveolar pressure in the lungs)). In some embodiments, the suction catheter 19 comprises an endotracheal tube cleaning member such that a single device provides suction and endotracheal tube cleaning. However, in accordance with several embodiments, such a single device may not be possible for pediatric or neonatal-sized endotracheal tubes due to size constraints.

FIG. 2 illustrates an embodiment of an endotracheal tube cleaning device 20, which may form a module that can be reversibly or removably coupled to the manifold 13 similar to the suction catheter device module 12. The endotracheal tube cleaning device module 20 and the suction catheter device module 12 may be interchangeable to facilitate more effective cleaning by using both suction and wiping cleaning mechanisms to clear out the endotracheal tube instead of suction alone. The endotracheal tube cleaning device 20 may include a syringe 21, a proximal connector 22, a sheath 23, an elongate shaft 24, an extension member (e.g., proboscis) 25 and a distal connector 26. The proboscis 25 is advantageously constructed to provide a close-fitting column through which the flexible catheter shaft 24 of the endotracheal tube cleaning device 20 may be passed and shall be of a sufficient length to provide column strength support from the exterior. In addition, the proboscis 25 is advantageously constructed to have an exterior surface area sufficient to collect the protective sheath 23. The protective sheath 23 is advantageously constructed to be substantially flexible and pliable and thus tends to collect in such a way that it would interfere with the insertion of the substantially flexible catheter shaft 24 of the endotracheal tube cleaning device 20. The proboscis 25, provides additional column strength for the flexible catheter shaft 24 of the endotracheal tube cleaning device 20 as well as a collection area to prevent interference from the protective sheath 23. As shown, the outer diameter of the proboscis 25 increases from its proximal end to its distal end (forming an overall frustoconical shape). The syringe 21 provides inflation or other expansion of a distal cleaning member (e.g., wiper) 27, the outside diameter of which is small enough to insert into and clean the lumen of an endotracheal tube as small as 2.0 to 2.5 mm. In some embodiments, the syringe 21 is color-coded to the size of the endotracheal tube and the size of the endotracheal tube is printed or otherwise included somewhere on the device 20 (e.g., at the connection of the syringe 21 to the elongate shaft 24). A hole 28 in a barrel of the syringe 21 allows precise control of the air volume sent through a pilot channel (not shown in FIG. 2 but shown in FIGS. 3A and 3B) of the elongate shaft 24 of the cleaning device 20 to the distal cleaning member 27. In some embodiments, the syringe 21 is permanently adhered to the proximal connector 22 to prevent syringes of differing volumes from being inadvertently connected to the elongate shaft 24. In other embodiments, the syringe 21 is removable from the proximal connector 22.

The elongate shaft 24 of the cleaning device 20 includes a pilot channel 32 (shown in FIGS. 3A, 3B) for inflation or other expansion of the cleaning member 27 and may have additional channels for other purposes (e.g., irrigation, photodynamic light therapy, visualization, suction or aspiration, delivery of drugs, anti-microbials or other therapeutics). In accordance with several embodiments, the elongate shaft 24 is advantageously co-extruded with an element or material that differs in composition from the elongate shaft 24 itself in order to achieve various purposes, such as column strength and pushability, curvature, limited stretch, light transmission or other desired characteristics. The endotracheal tube cleaning device 20 may incorporate any of the structural or functional features of the corresponding devices or components (e.g., cleaning devices 3210, 4110) described and/or illustrated in PCT Publication No. WO 2015/187583 and/or the devices described and/or illustrated herein. Although described herein as being inflatable, the cleaning member 27 may be expanded by non-inflatable means. For example, in some embodiments, the cleaning member 27 can incorporate any of the mechanically-expandable cleaning members or other cleaning members disclosed in U.S. Publ. No. 2011/0023885, U.S. Publ. No. 2013/0104884, and PCT Publ. No. WO 2011/126812, the entireties of each of which are hereby incorporated by reference herein, such as a mechanically-actuated scaffold (e.g., a mesh scaffold actuated by movement of two concentric tubes attached to opposite ends of the mesh scaffold with respect to each other). The endotracheal tube cleaning device 20 may be adapted for use with neonate-sized, pediatric-sized or adult-sized endotracheal tubes. The sheath 23 and proboscis 25 may be optional and only included for closed systems.

Figure 2A:
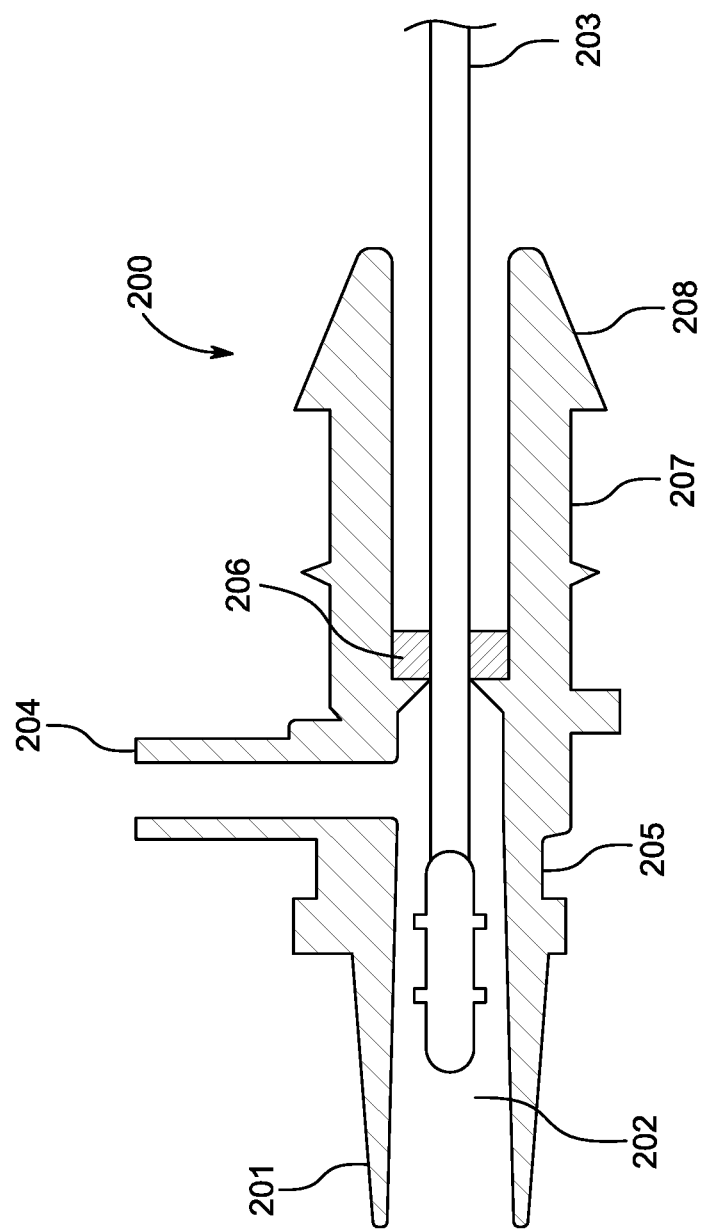
FIG. 2A illustrates a cross-section view of an embodiment of a connector (e.g., distal connector of the cleaning device of FIG. 2) adapted to couple to an endotracheal tube or manifold.

FIG. 2A illustrates a cross-section view of an embodiment of a connector 200 (e.g., distal connector 26 of cleaning device 20 of FIG. 2) adapted to removably couple to an endotracheal tube (e.g., endotracheal tube 14) or a manifold (e.g., manifold 13) via friction-fit engagement. The connector 200 includes a distal connection member or end portion 201 having a tapered profile or configuration (e.g., conical shape) with an outer diameter sufficient to reliably engage the endotracheal tube or manifold such that there are no leaks (e.g., air leaks or pressure leaks) or unintended disconnections. The outer cross-sectional dimension of the distal connection member or distal end portion 201 decreases from proximal to distal and the inner cross-sectional dimension increases from proximal to distal. The connector 200 includes a conical cavity or area 202 inside the tapered distal connection member 201 adapted to allow a catheter of a cleaning device 203 (e.g., elongate shaft 24 of cleaning device 20 with cleaning member 27) to be fully retrieved and the biofilm collected without worrying about collected biofilm being scraped off from the cleaning device (e.g., from cleaning member 27) while the cleaning device 203 is pulled back into the connector 200. The connector 200 may also include a flush port 204 adapted for rinsing the cleaning device with a syringe or other fluid filled device under pressure to remove debris retrieved by the cleaning device and retained inside the cavity 202. The generally conical shape of the area 202 (with the inner diameter being larger at the distal end than at the proximal end where the flush port 204 branches off) advantageously allows the pressure gradient of irrigation to be highest at the flush port 204 and lowest at the distal terminus. This pressure gradient helps move the debris from the narrowest part of the conical area 202 to the outside of the connector 200 through the opening at the distal tip of the connector 200. The connector 200 may optionally include a notch, groove, indentation or other retention feature 205 on an area on the outside diameter of the connector 200 adapted to retain a tethered cap or other tethered part (not shown). A circumferential seal 206 (e.g., valve, diaphragm) is included in a main lumen of the connector 200 that is adapted to prevent leaks in the ventilatory circuit and to wipe the elongate shaft (and/or cleaning member) of the cleaning device (or other instrument) clean upon retrieval back into the connector 200. For use in a closed system, the connector 200 includes an area (e.g., slot 207) on its outside diameter adapted to receive and retain at least a distal portion of a protective sheath (e.g., sheath 23). In some embodiments, a proximal end 208 of the connector 200 is sized and shaped to mount an extension member, or proboscis (e.g., extension member 25).

In accordance with several embodiments, the connector 200 facilitates collection of retrieved biofilm (e.g., debris, secretions), thereby minimizing the biofilm left behind after a therapeutic or diagnostic procedure (e.g., cleaning, clearing, wiping, visualization procedure). In some systems, the system (e.g., connector 200, cleaning device 20) is designed to be flushed under pressure for cleaning and reuse of the system on the same patient over an extended period of time (e.g., 24-72 hours).

Figure 2B:
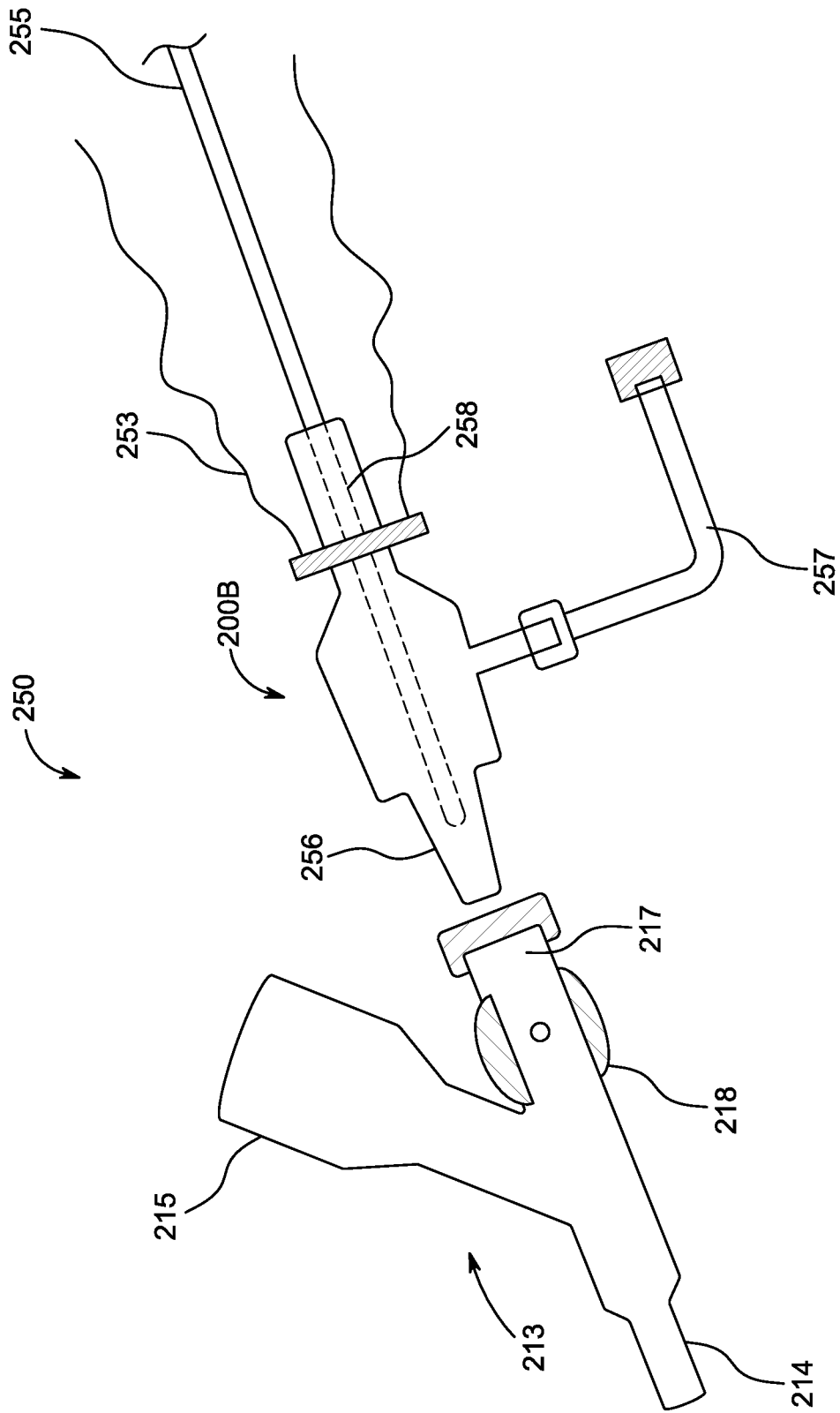
FIG. 2B illustrates an embodiment of a system that includes a cleaning device catheter module and a manifold, wherein the system is adapted to allow interchangeable connection of modules without loss of pressure or a break in ventilatory circuit.

FIG. 2B illustrates an embodiment of a system 250 that includes a cleaning device module 255 (e.g., cleaning devices or modules 12, 20) and a manifold 213, wherein the system 250 is adapted to allow interchangeable connection of catheters or modules (e.g., suction catheter module, bronchoscopic module, bronchoalveolar lavage catheter module, integrated suction and wiper cleaning catheter module, endotracheal tube cleaning device module, etc.) without loss of pressure or a break in ventilatory circuit.

The manifold 213 includes a distal connection member 214 adapted to couple to or interface with an endotracheal tube or other body-inserted tube (neonatal size, pediatric size or adult size). The manifold 213 also includes a rotatable or otherwise-actuated stopcock 218 adapted to shut or close off an instrumentation port 216 of the manifold 213 from the ventilatory circuit connected to the ventilator port 215. The stopcock 218 may incorporate any of the structural and/or functional features of the manifold occluder 18 described herein. The cleaning device module 255 includes a distal connector 200B (e.g., distal connector 26, 200) and a protective sheath 253 (e.g., sheath 23). The distal connector 200B includes a distal connection member or distal end portion 256, a flush port 257 (e.g., flush port 204) and an extension member or proboscis 258 (e.g., extension member or proboscis 25). The illustrated distal connection member or distal end portion 256 comprises a conical-shaped connection member adapted to removably couple to the manifold 213. Although illustrated as a closed catheter module, the cleaning device module 255 may be interchanged with another closed or open cleaning module or diagnostic module (e.g., suction catheter module, bronchoscopic module, bronchoalveolar lavage catheter module, integrated suction and wiper cleaning catheter module, endotracheal tube cleaning device module, etc. such as described herein or in WO 2015/187583, the entire contents of which is hereby incorporated by reference herein.

In accordance with several embodiments, the system 250 described in connection with FIG. 2B advantageously facilitates modular connections of small diameter devices into a ventilatory circuit such that dead space is minimized and cleaning/flushing of devices (e.g., cleaning or suction catheters or visualization devices) can be performed in real-time without exposing the patient to negative pressures and/or without disconnecting the patient from a ventilator circuit. The conical-shaped connection member or distal end portion 256 to the stopcock 218 may advantageously be designed (e.g., shaped and sized) to fully engage the manifold through the stopcock 218, thereby reducing (e.g., minimizing) dead space and providing a reservoir for collection of biofilm (e.g., debris, secretions) removed from the endotracheal tube or other body-inserted tube, in accordance with several embodiments. The system 250 may be used for neonate-sized, pediatric-sized or adult-sized endotracheal tubes and modules.

FIGS. 3A AND 3B illustrate a portion of an embodiment of the elongate shaft 24 that includes a coextruded material 30 of a different material than the material of the elongate shaft 24 (before and after a curing process, respectively). In some embodiments, the coextruded material 30 (and thus the elongate shaft 24) may be manufactured to have a natural curved configuration after a curing process. In accordance with several embodiments, the curvature of the catheter shaft 24 is beneficial, desirable, and incorporated into the coextrusion process so as to produce an intentional curve to the cleaning device. The curvature may facilitate introduction into ports of manifolds or into particular airways of the trachea-bronchial tree. In some embodiments, the natural curvature is achieved by a specially-controlled co-extrusion process for silicone or other material over a solid or twisted member and a curing process for the silicone or other material which biases the extrusion in a particular curvature direction advantageous for insertion into a similarly curved tube (e.g., an endotracheal tube). FIGS. 3A and 3B illustrate the one or more channels 32 (e.g., a pilot channel for inflation and/or other accessory channels) extending along the length of the elongate shaft 24. In some embodiments, the catheter shaft 24 comprises an extruded silicone catheter; however, other materials may be used as desired and/or required. The coextruded material 30 may comprise a wire that is co-extruded with at least a portion of the length of the shaft 24 of the catheter and is adherent to the shaft along its length. In one embodiment, the wire is braided. As shown in the illustrated embodiment, the wire does not extend all the way to the distal tip of the catheter in order to prevent possible injury that might be caused by the wire should it protrude from the distal tip of the catheter during use. In some embodiments, the wire provides, facilitates or increases pushability to the catheter as it is inserted and prevents or otherwise reduces stretching or snapback when the catheter is removed from a body-inserted tube (e.g., endotracheal tube). In other embodiments, a solid wire or mandrel may be coextruded to provide increased pushability and malleability. In some embodiments, a flexible tube (nylon, Teflon, PEEK, polyamide, etc.) may be used to provide or increase pushability, prevent or reduce stretch or snapback and provide an alternate fluid path for delivery of medicaments (chlorhexidine) or fluids (saline). The coextrusion may be particularly advantageous for small diameter, flexible catheters (such as silicone catheters designed for neonate or pediatric patients). If improved pushability is not required or desired, the catheter shaft 24 may be coextruded over another stretch-limiting material, such as suture, string, filament or other material. Additional details regarding coextrusion may be found in PCT Publication No. WO 2015/187583 (see, e.g., Paragraphs [0043], [0149], [0158], [0165] and [0185]) and/or as otherwise described herein.

Figure 4:
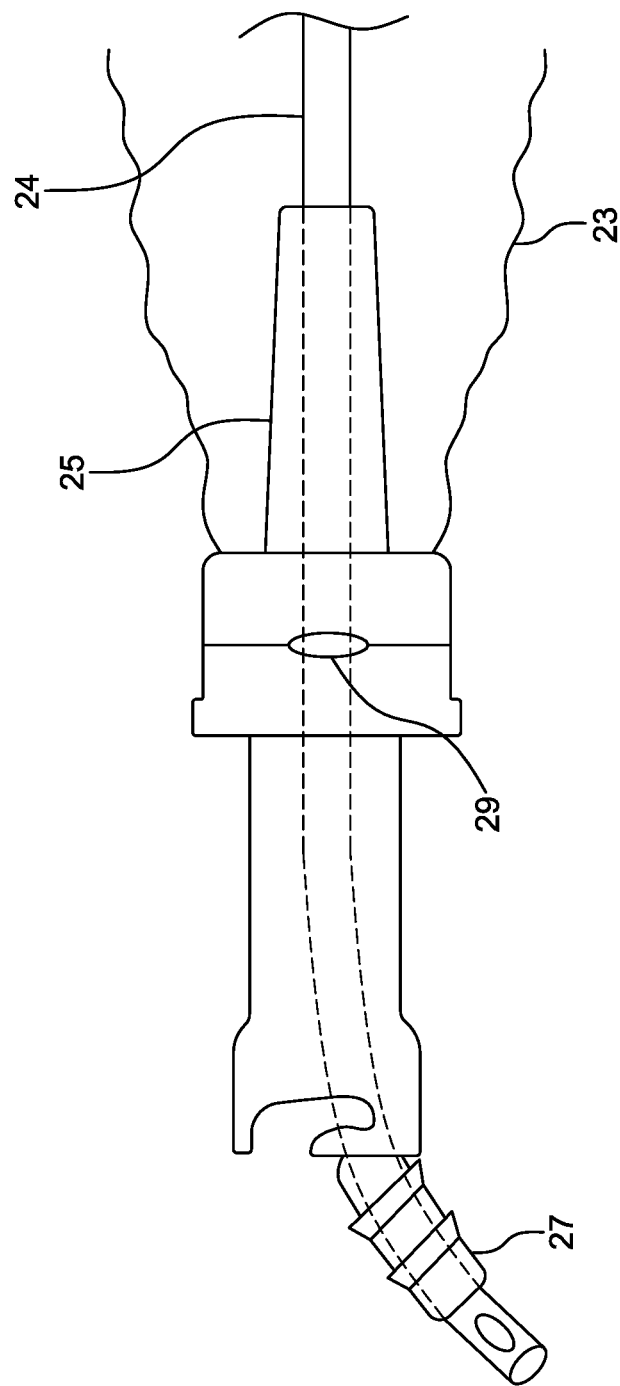
FIG. 4 illustrates a close-up view of the distal end portion of the cleaning device module of FIG. 2 that shows the tubular extension (or proboscis) extending into the sheath.

FIG. 4 illustrates a close-up view of the distal end portion of the cleaning system of FIG. 2 that shows the extension member, or proboscis, 25 extending into the sheath 23. The extension member 25 (which may be tubular or cone-shaped in various embodiments) may extend from the distal connector 26 into the sheath 23 to advantageously allow for increased shaft column strength and pushability, as well as serving as a collection site for the collapsible sheath 23 as the elongate shaft 24 of the cleaning device 20 is inserted into the distal connector 26. The extension member 25 may also allow the sheath 23 to be pulled onto the distal connector, or collection tube, 26 and therefore pull the shaft 24 into the endotracheal tube as the sheath 23 is collected.

In accordance with several embodiments, the proboscis component provides additional column strength to a tube as that tube is pushed or inserted into another tube, cavity, valve, seal, orifice or other application where the soft nature of the inserted tube is desired for certain design or safety considerations (e.g., need for a silicone balloon for proximity to tissue or structures that might be damaged by a more rigid catheter) that renders the tube difficult to push due to a lack of column strength (e.g., the tube meets resistance and folds over onto itself or kinks). The additional column strength provided is related to the fit between the proboscis 25 and the catheter, as well as the length of the proboscis relative to the length of the catheter and different results can be achieved by changing these dimensions. In some embodiments, the proboscis 25 provides a mechanism to remove a protective sheath (e.g., sheath 23) out of interference from a catheter in the systems or devices described herein. For example, in many medical or industrial applications it is desirable to protect the user from contaminants in the system they are addressing with the device. A protective barrier (e.g., sheath) is desirable. In some embodiments, the sheath (e.g., sheath 23) can interfere with the insertion of a catheter because it tends to bunch or collect near the insertion point. As the sheath collects (e.g., bunches), the friction and resistance to insertion increases and in some cases hinders the insertion of a catheter (particularly if the catheter has low column strength). The proboscis may advantageously be used to collect the sheath and keep it from bunching around the catheter at the insertion point thereby reducing or eliminating resistance to insertion and allowing an otherwise unusable soft catheter to be utilized.

In some embodiments, a circumferential seal 29 (e.g., pucker valve or other diaphragm or valve or seal member) within the distal connector 26 is adapted to prevent air and secretions from collecting within the sheath 23. FIG. 4 also illustrates a pilot channel 40 for inflation extending along a length of the elongate shaft 24. Additional channels may be included as well (e.g., for irrigation, aspiration, fluid delivery, drug delivery, microbicidal delivery, light delivery, visualization scopes or devices).

Referring back to FIG. 2, the distal connector 26 may comprise a housing and a distal end portion (e.g., connection member) that is sized and adapted to fit into a port of a manifold connector (e.g., instrumentation port 17, 217 of manifold 13, 213, 613). The endotracheal tube cleaning device or module 20 may thus transiently or interchangeably replace a closed suction catheter (e.g., suction catheter device module 12) in order to clean the endotracheal tube or other body-inserted tube. In some embodiments, the endotracheal tube cleaning device or module 20 can be sized to transiently connect through a side port of a manifold (e.g., manifold 13, 213, 613) of a closed suction system (as described in connection with FIG. 1) to clean the endotracheal tube.

A flush port 280 connected to the distal connector 26 can be used to flush removed secretions from the cleaning member 27 out the end of the cleaning device 20. A tethered cap 281 can be used to maintain closure of the end of the cleaning device 20 (e.g., module) when off-line (e.g., when not coupled to a ventilator manifold). The cap 281 can advantageously be sized to also cap the closed suction catheter during the time it is removed from the manifold (e.g., manifold 13) and replaced by the cleaning device 20 (e.g., module).

Markings or indicia 260 may be provided or included on the elongate shaft 24 to help determine appropriate positioning within the endotracheal tube to be cleaned by matching the markings 260 to the ISO standard markings on the outside of the endotracheal tube.

Turning to FIG. 5, modular cleaning devices (e.g., closed suction catheters and/or endotracheal tube cleaning devices adapted to be removably coupled to ventilator manifolds) or other instrumentation (e.g., scopes) designed for insertion within body-inserted tubes may be stored off-line (e.g., remotely or at least not coupled to the manifold) for variable periods of time when not in use and not actively connected to the ventilator manifold. These catheters, instruments, cleaning devices, and scopes may be cleaned before being disconnected from the ventilator manifold by instilling or infusing saline or antimicrobial solutions into a flush port of the modular connector and suctioning the fluid out of the cleaning chamber until the device is visibly clean. However, the instruments may not be adequately cleaned by irrigation or flushing alone.

FIG. 5 illustrates an embodiment of a sterilization cap 50. In accordance with several embodiments, the sterilization cap 50 of FIG. 5 can be placed over the end of any module (e.g., suction catheter cleaning module 12, endotracheal tube cleaning device module 20, visualization device module, etc.) being disconnected from the ventilator manifold (e.g., manifold 13, 213, 613) of an airway maintenance system (e.g., system 10) for off-line storage such that the cap 50 can be used to sterilize the device (catheter, cleaner, scope, instrument) while the device is disconnected and stored. In accordance with several embodiments, use of such a sterilization cap 50 can advantageously prolong the time period that any module of the airway maintenance system may be used (e.g., 72 hours or longer).

In accordance with several embodiments, the sterilization cap 50 is advantageously sized and adapted to fit over the distal end of all modules and adapters with a positive engagement, thereby providing a "one-size-fits-all" solution. In the illustrated embodiment of FIG. 5, the module is shown as the endotracheal tube cleaning module 20 but could also be a closed suction cleaning module (e.g. suction catheter device module 12) or other module.

The sterilization cap 50 includes an on-off switch 51, one or more power sources 52, one or more light sources 53 and a window 54. In some embodiments, positive engagement is required before the function of the on-off switch 51 is able to be activated. The one or more power sources 52 may comprise disposable or rechargeable batteries or other power sources or energy storage devices (e.g., capacitors or other electrical or electrochemical energy storage devices). The one or more power sources 52 may also comprise a wired electrical source. For embodiments in which rechargeable batteries are contemplated, the sterilization cap 50 includes a recharge interface adapted to receive a charging component or mechanism. In some embodiments, the one or more light sources 53 comprise light-emitting diodes (LEDs). In embodiments in which ultraviolet wavelength LEDs are used for the light sources 53, the window 54 may comprise a quartz window adapted to allow the LEDs utilizing microbicidal UV-C wavelengths to deliver such light to the inside of the removed module, including to the catheter, scope or device inside. Although the quartz window 54 passes the UV-C light, the UV-C light is completely absorbed by the modular materials (e.g., plastic materials) such that no external UV-C energy is delivered to the external environment, the patients, or end users. In some embodiments, the sterilization cap 50 and the one or more light sources 53 are configured to provide photodynamic therapy. For example, a photodynamic therapy solution can be injected into the module to be cleaned and then the solution can be suctioned out so that the surfaces of the module to be cleaned are coated. The one or more light sources 53 may then be activated to sterilize the module.

In some embodiments, the one or more power sources 52 are chosen as needed to deliver the appropriate wavelength (e.g., 200 nm-280 nm, 200 nm-260 nm, 200 nm-240 nm, 220 nm-280 nm, 240 nm-280 nm, 220 nm-260 nm, overlapping ranges thereof, or any value within the recited ranges) for the appropriate amount of time (e.g., 1 second to 30 minutes, 1 second to 2 minutes, 1 second to 30 seconds, 5 seconds to 30 seconds, 10 seconds to 1 minute, 30 seconds to 90 seconds, 30 seconds to 2 minutes, 1 minute to 5 minutes, 2 minutes to 10 minutes, 5 minutes to 15 minutes, 10 minutes to 30 minutes, 15 minutes to 30 minutes, overlapping ranges thereof, or any value within the recited ranges) at the appropriate power or energy level in order to sterilize the catheter, device, and inside of the module. In some embodiments, the energy delivered is within a range of between 1 and 150 mJ/cm$^2$ (e.g., between 1 and 25 mJ/cm$^2$, between 10 and 50 mJ/cm$^2$, between 50 and 100 mJ/cm$^2$, between 50 and 150 mJ/cm$^2$, between 1 and 100 mJ/cm$^2$, between 10 and 100 mJ/cm$^2$, overlapping ranges thereof, or any value within the recited ranges). In embodiments where batteries are used for the one or more power or energy sources, the sterilization cap 50 may be configured to provide an indication or alert to a user that a battery change or charge is required. The sterilization cap 50 may thus include one or more indicator lights or audible sound or tactile haptic outputs.

The on-off switch 51 may optionally include a timer to control a duration of time that the sterilization cap 50 is providing active sterilization. The timer can be set to a specific amount of time according to the requirements for sterilization. In some embodiments, the on-off switch 51 may be able to be turned on only when the cap 50 is positively engaged with the module to be sterilized. The on-off switch 51 may be advantageously designed so that it can be activated after the cap 50 and module have been placed into an off-line (e.g., off-site, or remote) storage bag. In some embodiments, the on/off function is automatically triggered by the positive engagement of the cap 50 with the module as described above. In some embodiments, there is an indicator light to alert the user that the device is functioning. In some embodiments, there is an indicator light (which may be the same light as the device functioning indicator light or a different light) to alert the user that the cleaning cycle is complete. The indicators may alternatively or additionally provide an audible indication and/or a vibratory haptic indication.

FIGS. 5 and 5A illustrate two different embodiments of the window 54. As shown in FIG. 5A, the sterilization cap 50, the window 54 of the cap 50 may include projections or protuberances 55 adapted to project or protrude and extend into the inside of the module being sterilized if needed to more effectively sterilize the module and device. The window 54 may be advantageously constructed to include prongs, tubes or other structures as shown by the illustration in FIG. 5A so as to provide a mode of transmission for the UV-C light emitted into a cavity and surrounding surfaces of a device inside of a module (e.g., endotracheal tube cleaning module 20) that may be perpendicular to the one or more light sources 53 (e.g., LEDs). Such construction is advantageous to faster and more complete sterilization of such a device. In some embodiments, the projections 55 may be a tube or plurality of tubes (e.g., quartz cones or tubes). In some embodiments, mirrored surfaces may be used to transmit (e.g., reflect) light to otherwise unreachable portions of the targeted cleaning area (e.g., cavity of a portion of a module or device).

Figure 9:
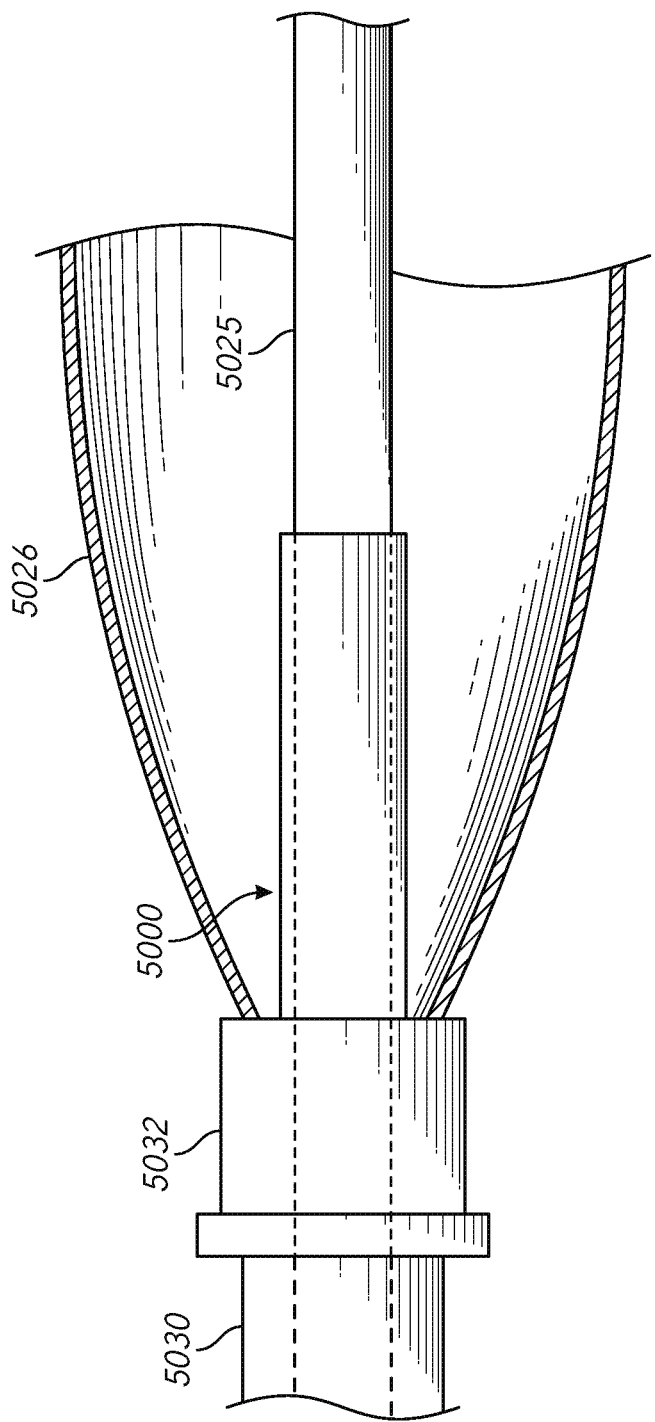
FIG. 9 illustrates an embodiment of a tubular, or cap, extension member configured for use with a suction system.

FIG. 9 illustrates an embodiment of a cap extension member 5000 configured for use with a closed system module (e.g., suction catheter device cleaning module 12 or endotracheal tube device cleaning module 20). The cap extension member 5000 may be formed integral with or removably coupled to a cap 5032 that confines a flexible sheath 5026 surrounding a suction catheter 5025 at the point of the sheath's connection to a ventilating manifold 5030. The cap extension member 5000 may be injection molded as part of the manifold 5030 or molded separately. The cap extension member 5000 may be formed with a receptacle for mechanically attaching to the cap 5032. The cap extension member 5000 may be extruded of a material suitable for plastic bonding (e.g., PVC) and may be bonded to the cap 5032 using solvent (e.g., cyclohexanone) or adhesive (e.g., cyanoacrylate). The cap extension member 5000 comprises a shaft having a length configured to extend into the flexible sheath 5026. The cap extension member 5000 may be composed of a lightweight and transparent material. For example, the cap extension member 5000 may be composed of nylon, PEEK, Teflon, polyamide, PVC, etc. In accordance with several embodiments, the cap extension member 5000 advantageously allows an operator to "pull" the suction catheter 5025 into the manifold 5030 and body-inserted tube by sliding the sheath 5028 proximally over the shaft of the extension member 5000 rather than requiring "pushing" of the catheter 5025 through the cap 5032.

In accordance with several embodiments, the catheter 5025 may be of such a small diameter as to limit its column strength to such a point that it is impossible to push as the catheter 5025 will simply fold over on itself. Utilizing cap extension member 5000, it is possible to pull the catheter 5025 rather than push it. As the flexible sheath 5026 is pulled on the cap extension member 5000 and collected, the flexible sheath 5026 creates a pulling force that allows the catheter 5025 to advance without folding over on itself. Further, the cap extension member 5000 allows the flexible sheath 5026 to be moved out of the way of the catheter 5025 such that it prevents the bunching up of the flexible sheath 5026 from interfering with the advancement of the catheter 5025.

In accordance with several embodiments, the cap extension member 5000 may advantageously allow suction catheters that are soft, pliable, or extremely flexible and have limited pushability to be employed, as well as suction catheters having smaller diameters (e.g., between 1 mm and 5 mm). For example, the cap extension member 5000 may facilitate introduction of soft, pliable catheters having integrated expandable cleaning members that are designed for cleaning of body-inserted tubes sized for neonates or pediatric patients. The cap extension member 5000 may also be incorporated in systems without the accessory cap 4955, 4855. For example, a tubular extension member operating in the same manner as the cap extension member 5000 described herein may be used in connection with any manifold or adapter (or port of a manifold or adapter) for the insertion of soft, pliable catheters or instruments and/or or instruments with diameters less than 5 mm (e.g., 2.5 mm) in outer diameter. The extension member (e.g., proboscis) 25 described herein may incorporate any of the structural or functional features of the cap extension member 5000.

FIGS. 10A and 10B illustrate an embodiment of a suction catheter that includes an endotracheal tube cleaning portion 3210 along or near its distal end. For pediatric and/or neonatal patients, a suction catheter having an expandable endotracheal tube cleaning member disposed thereon likely cannot be used to clean an endotracheal tube sized for such patients (e.g., less than 7 mm, less than 5 mm) due to size limitations, in accordance with several embodiments. However, the structural and functional features described in connection with FIGS. 10A, 10B and 11A-11C related to the endotracheal tube cleaning portion and the suction catheter cleaning device 3200 may be incorporated into the cleaning member 27 and the endotracheal tube cleaning device module 20 described herein instead of being used on a suction catheter. The suction catheter device 3200 may also be used for adult-sized endotracheal tubes (e.g., 7 mm or greater).

In some embodiments, the catheter body 3204 of the device 3200 comprises one or more side suction holes, openings or ports 3220, 3224 (e.g., distal alone (3220), distal and proximal (3220 and 3224), or proximal alone (3224)) distal and/or proximal to the cleaning device 3210, as desired or required. Such side holes, openings or ports 3220, 3224 are configured to be in fluid communication with one or more internal fluid passageways of the catheter body 3204. Further, the distal end 3228 of the catheter device can be at least partially open and in fluid communication with an interior passage of the catheter body 3204. Thus, suction can be accomplished along one or more different locations of the suction catheter. The number, size, and positioning of the suction holes, openings, or ports may be variably altered as part of the suction catheter design and manufacture in order to direct varying degrees of suction at specific locations along the suction catheter 3204. In addition, varying amounts of suction may be applied to the proximal and distal ports 3220, 3224. Such variations may be required depending on the overall dimensions and diameter of the suction catheter 3204 and the amount of suction (in mm Hg) intended for delivery at the suction holes, openings, or ports 3220, 3224, thereby allowing for dynamic suction control. In accordance with several embodiments, a suction catheter device comprising suction holes, openings, or ports 3220, 3224 both proximal and distal to the cleaning portion 3210 advantageously facilitates suction on both sides of the cleaning portion 3210. Suction holes, openings, or ports 3224 positioned proximal to the cleaning portion 3210 advantageously facilitate suction (and removal) of biofilm or other debris removed by the cleaning portion 3210 (e.g., cleaning members or wipers 3240) while the suction catheter device is being withdrawn, and may be the only source of suction if the main suction lumen of the suction catheter device 3200 is occluded by members of the cleaning portion 3210 (such as balloons).

As depicted In FIGS. 10A and 10B, the wiper or cleaning portion 3210 can comprise one or more distensible or extendable wiper members 3230, such as, for example, an expandable sleeve, ring or balloon. Such balloons or other distensible members 3230 can be configured to be moved between a collapsed position, where they remain adjacent the catheter body 3204 to which they are secured (as shown in FIG. 10A), and an expanded position, where they move away from the central axis and the outer diameter of the catheter body 3204 (as shown in FIG. 10B). As shown, in some embodiments, the cleaning portion 3210 is configured to at least partially contact the inside surface of a body-inserted tube (e.g., endotracheal tube) when the balloon or other distensible or expandable member 3230 is in the radially-expanded position. Accordingly, as the device 3200 is withdrawn (e.g., retracted rearwardly from inside the endotracheal tube or other body-inserted tube), biofilm and/or other debris is removed from within the tube. As shown in FIG. 10B, fluid or other air used to selectively expand the balloon or other distensible member 3230 can be routed to the interior of the balloon or other distensible member 3230 through one or more fluid passages 3260 of the catheter body 3204 and/or another interior portion of the catheter device 3200. In some embodiments, the wiper or cleaning portion 3210 is comprised of silicone of 50 A-70 A durometer.

With continued reference to FIGS. 10A and 10B, the cleaning portion 3210 of the catheter device 3200 comprises one or more cleaning, wiping or shearing members 3240 that are configured to engage and contact the inside wall of the body-placed or body-inserted tube (and/or the biofilm or other debris that has collected therein). For example, in the illustrated embodiment, the balloon or distensible member 3230 consists of a total of two shaving rings or cleaning members 3240. Such rings or other cleaning members 3240 can extend completely or partially around the circumference of the cleaning portion 3210, as desired or required. The rings or other cleaning members 3240 can have generally square or sharp (e.g., approximately 90°) edges. However, in other embodiments, the cleaning members 3240 comprise more rounded (non-sharp or smooth) profiles. Further, in other embodiments, the cleaning portion 3210 comprises more (e.g., 3, 4, 5, more than 5, etc.) or fewer (e.g., 1) rings or other cleaning members 3240. The balloon or distensible member 3230 (and thus the cleaning portion 3210) is expanded (e.g., to engage the inside wall of the body inserted tube and/or the debris accumulated thereto) by selectively delivering a volume of fluid (e.g., air) to the balloon or distensible member 3230 via one or more "pilot channels" or air or fluid injection channels 3260 attached to or within the catheter device 3200.

According to some embodiments, the balloon or other distensible member 3230 is secured to the adjacent catheter body 3204 using any attachment method or device, as desired or required. For example, in the arrangement illustrated in FIGS. 10A and 10B, the balloon 3230 is connected to the catheter body 3204 using one or more adhesive joints 3236. Such adhesions or other joints can be located, either intermittently or continuously, along any distal, proximal and/or central portion of the balloon 3230. In some embodiments, the cleaning portion 3210 (e.g., balloon 3230, cleaning members 3240) and adjacent catheter body 3204 are composed (partially or entirely) of silicone and the adhesive joint is achieved with silicone adhesive.

According to some embodiments, the balloon 3230 and/or sleeve member comprises a generally soft material with memory and recoil characteristics such that when fluid or air is withdrawn from the balloon 3230, the cleaning portion 3210 returns to its collapsed position, immediately adjacent the suction catheter body 3204. In some embodiments, the balloon, wiper or sleeve member comprises a smooth surface along a portion of or the entire length and does not comprise any shaving rings or cleaning members. The balloon, wiper or sleeve member may comprise one or more of urethane, silicone, PEBAX thermoplastic elastomer, or PVC materials. In some embodiments, the balloon, wiper or sleeve member is comprised of silicone of 50 A-70 A durometer.

In some embodiments, such a catheter device 3200 is used for suction only without expansion of the cleaning portion 3210 (e.g., if used as suction catheter cleaning device module 12 in system 10 described above). Alternatively, the device 3200 can be utilized without suction and with only expansion of the cleaning portion 3210, as desired or required. In other embodiments, such devices 3200 advantageously enable a user to perform both (e.g., simultaneous) suctioning and cleaning of the body-inserted tube (e.g., endotracheal tube) via expansion of the cleaning portion 3210 and balloon or other distensible member 3230. In other embodiments, when the catheter device 3200 is withdrawn from the body inserted tube after expansion of the cleaning portion 3210, biofilm or other debris removed from the inside walls of the body-inserted tube that has collected proximally to the cleaning portion 3210 is removed by the application of suction to proximal suction ports 3224. In some embodiments, the suction ports 3220, 3224 may be designed (e.g., by varying the size, position, number, and suction pressures) to provide dynamic control of suction distal and/or proximal to the cleaning portion 3210. In one embodiment, when the balloon or other distensible member 3230 is expanded and suction is applied, only the proximal suction port(s) 3224 are activated.

FIGS. 11A-11C illustrate various views of the suction catheter device 3200 positioned within a body-inserted tube (e.g., endotracheal tube) and is provided to show how the cleaning device 27 of endotracheal tube cleaning device 20 could operate as well. As discussed herein, the devices 20, 3200 can be used in a closed suction system. For example, the device 20, 3200 can be configured to retract within a flexible enclosure, either with or without a manifold (e.g., manifold 13, 213, 613). In such systems, the catheter device 20, 3200 can be selectively retracted into a sleeve or sheath. Accordingly, the biofilm, other debris and/or other unwanted materials removed from the subject being treated can be safely maintained within the sleeve and away from the exposed external environment, thereby allowing the clinician to reuse the device over a particular time period. Further, as discussed, the clinician is provided with great flexibility when using such a device 3200, as he or she can choose to use the device 3200 for suction only, for body-inserted tube cleaning only, for cleaning of portions of the respiratory tract or tree, and/or combinations thereof, as desired or required.

In several embodiments, the proximal controllers of the suction catheter device 3200 described herein independently controls the suction and cleaning portion activation (e.g., expansion) functions, thereby allowing the suction to function independently, the cleaning portion to be activated and function independently, or neither suction nor the cleaning portion to be activated, as desired or required. In some embodiments, the proximal controller or control unit comprises a locking mechanism to prevent inadvertent activation of the suction and/or deployment of the expandable cleaning portion. The locking mechanism may advantageously be easy to use and to interpret, thereby reducing user error and improving user satisfaction. Unintended activation of the suction could significantly decrease ventilator circuit pressures, volumes, and/or flows, each of which may potentially cause significant adverse effects on an intubated patient. Unintended deployment of the expandable cleaning member or portion could significantly obstruct the artificial airway (e.g., endotracheal or other body-inserted tube), which could potentially cause significant clinical deterioration if left deployed for an extended period of time. In some embodiments, the locking mechanism is incorporated into the proximal controller or control unit. A portion (e.g., operational guide) of the proximal controller or control unit may be rotational or otherwise transitional in 1, 2 or 3 steps or detents. For example, the operational guide may rotate between three rotation positions each corresponding to a different operational state. In such embodiment, the initial position corresponds to an operational state in which suction and activation of the cleaning member are both locked or prevented, the second position corresponds to an operational state that allows suction only (with activation of the cleaning portion being locked or prevented), and the third position corresponds to an operational state that allows activation of the cleaning member only (with suction being locked or prevented). In this embodiment, risk of severe negative pressures and major atelectasis can be minimized or otherwise reduced. The transitions between the positions may be effected by rotation or other transitional movement. For rotational embodiments, continued rotation beyond the third position may cause transition back to the first position in a full circle. In various embodiments, the operational guide advantageously facilitates audible, visual and/or tactile confirmation of a transition between operational states or positions. In some embodiments, both suction and cleaning member activation are prevented when the operational guide is in a transition between the first, second or third positions. The locking mechanism may prevent suction in the initial position, prevent activation (e.g., expansion) of the cleaning member in the second position and prevent suction in the third position. The positions and corresponding functions are interchangeable in various embodiments. In some embodiments, only two operational states exist (suction only and combined suction and cleaning member operation).

Although the cleaning devices, methods, and systems described herein have been described in connection with the cleaning of endotracheal tubes or other body-inserted tubes or with the suctioning of distal airways of a patient, the embodiments and features described herein can be used for other medical applications, such as, for example, urologic applications; endoscopy, laparoscopic applications, orthopedic and spine applications, and for tubes within the body such as dialysis grafts.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the embodiments herein disclosed should not be limited by the particular disclosed embodiments described above.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Additionally, the skilled artisan will recognize that any of the above-described methods can be carried out using any appropriate apparatus. Further, the disclosure herein of any particular feature, aspect, method, property, characteristic, quality, attribute, element, or the like in connection with various embodiments can be used in all other embodiments set forth herein. Additionally, process steps may be added, removed, or reordered. The ranges disclosed herein encompass any and all overlap, subranges, and combinations thereof, as well as individual numerical values within that range. For example, description of a range such as from about 4 mm to about 7 mm should be considered to have specifically disclosed subranges such as from 4 to 6 mm, from 5 to 7 mm, etc., as well as individual numbers within that range, for example, 4, 5.5, 6, 6.5, 7 and any whole and partial increments therebetween. Language such as "up to," "at least," "greater than," "less than," "between," and the like includes the number recited. Numbers preceded by a term such as "about" or "approximately" include the recited numbers. For example, the terms "approximately", "about", and "substantially" as used herein represent an amount close to the stated amount that still performs a desired function or achieves a desired result.

For purposes of this disclosure, certain aspects, advantages, and novel features of the inventions are described herein. It is to be understood that not necessarily all such advantages may be achieved in accordance with any particular embodiment of the invention. Thus, for example, those skilled in the art will recognize that the inventions may be embodied or carried out in a manner that achieves one advantage or group of advantages as taught herein without necessarily achieving other advantages as may be taught or suggested herein.

NON-LIMITING EXAMPLES OF EMBODIMENTS

Embodiment 1: A connector interface comprising a distally-tapered outside end and a proximally-tapered conical inside end for collection, retention, and irrigation cleaning of debris removed from a tube by a catheter or other instrument inserted through the connector interface.

Embodiment 2: An endotracheal tube connection manifold comprising a distal end endotracheal tube connection and proximal connections for ventilation and access for interchangeable catheters, comprising a shutoff valve to the catheter side that substantially eliminates dead space in the ventilatory circuit and facilitates cleaning of the catheters without losing tidal volume or positive end expiratory pressure.

Embodiment 3: A microbicidal UVC device adapted to removably couple to a catheter or other device, comprising a proximal end having a UVC source and a coupling mechanism adapted to removably couple to the catheter or other device.

The device of Embodiment 3, further comprising one or more of the following:
 a) a coupling mechanism adapted to prevent energy or light emission when not connected to a catheter or other device for cleaning;
 b) an integrated timer for assuring proper energy or light emission;

c) an indicator light adapted to indicate when the device is active and/or when a light delivery cycle is complete;
d) a recharging interface;
e) a low power indicator; and/or
f) quartz protuberances (e.g., cones) for transmission of UVC light deeper into the catheter or other device housing.

What is claimed is:

1. A system for maintenance of an endotracheal tube having an external diameter of less than 5 mm, the system comprising:
    a manifold comprising:
        a ventilation port configured to be removably coupled to a ventilator,
        an access port configured to be removably coupled to multiple modules adapted to access and/or treat an artificial airway through the manifold, and
        a distal port configured to be removably coupled to the artificial airway, wherein the ventilation port and the access port branch off from the manifold to form a Y shape;
    an occluder positioned at or near a location along a length of the manifold at which the ventilation port and the access port branch off from a main body of the manifold, wherein the occluder is configured to transition between an open configuration and a closed configuration;
    a suction catheter module configured to be removably coupled to the access port of the manifold and comprising a suction catheter configured to be introduced into the artificial airway through the manifold and to suction out accumulated biofilm from the artificial airway; and
    an artificial airway cleaning device module configured to be removably coupled to the access port of the manifold and comprising a sterilization device, the sterilization device comprising:
        a proximal end having an ultraviolet-C (UV-C) light source;
        a coupling mechanism adapted to removably couple to the suction catheter or other device; and
        a power switch adapted to prevent light emission when the sterilization device is not coupled to the suction catheter or other device.

2. The system of claim 1, wherein the sterilization device comprises a cap configured to be coupled to the access port of the manifold.

3. The system of claim 1, wherein the sterilization device comprises at least one projection adapted to project inside of the manifold.

4. The system of claim 3, wherein the at least one projection comprises a quartz protuberance adapted to transmit UV-C light deeper into the manifold.

5. The system of claim 1, wherein the sterilization device further comprises one or more power sources that power the UV-C light source.

6. The system of claim 1, wherein the UV-C light source of the sterilization device is configured to provide photodynamic therapy.

7. The system of claim 1, wherein the power switch of the sterilization device is automatically triggered by positive engagement of the sterilization device to the suction catheter or other device.

8. The system of claim 4, wherein the quartz protuberance is adapted to project or protrude and extend into the suction catheter or other device.

9. The system of claim 4, wherein the quartz protuberance provides a mode of transmission of UV-C light into the suction catheter or other device that is perpendicular to the UV-C light source.

* * * * *